United States Patent
Bochner (10) Patent No.: US 6,436,631 B1
(45) Date of Patent: *Aug. 20, 2002

(54) COMPARATIVE PHENOTYPE ANALYSIS FOR ASSESSMENT OF BIOLOGICALLY ACTIVE COMPOUNDS SUCH AS ANTIMICROBIALS

(75) Inventor: Barry Bochner, Alameda, CA (US)

(73) Assignee: Biolog, Inc., Hayward, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/776,332

(22) Filed: Feb. 2, 2001

Related U.S. Application Data (63) Continuation of application No. 09/556,898, filed on Apr. 20, 2000.

(51) Int. Cl.⁷ .............................. C12Q 1/00; C12Q 1/02; C12Q 1/18; C12N 1/00
(52) U.S. Cl. .............................. 435/4; 435/29; 435/975; 435/32; 435/822
(58) Field of Search ............................. 435/4, 29, 975, 435/32, 822

(56) References Cited

U.S. PATENT DOCUMENTS

| | | |
|---|---|---|
| 3,107,204 A | 10/1963 | Brown et al. |
| 3,197,384 A | 7/1965 | Goldman |
| 3,935,067 A | 1/1976 | Thayer |
| 3,963,442 A | 6/1976 | Bullard et al. ................ 435/4 |
| 4,076,592 A | 2/1978 | Bradley |
| 4,326,052 A | 4/1982 | Kang ............................ 435/4 |
| 4,326,053 A | 4/1982 | Kang et al. ................... 435/4 |
| 4,343,782 A | 8/1982 | Shapiro |
| 4,603,108 A | 7/1986 | Bascomb |
| 4,604,351 A | 8/1986 | Amaral |
| 4,856,073 A | 8/1989 | Faber et al. |
| 5,063,090 A | 11/1991 | Wannlund |
| 5,164,301 A | 11/1992 | Thompson et al. |
| 5,188,965 A | 2/1993 | Wannlund |
| 5,223,402 A | 6/1993 | Abbas et al. |
| 5,340,747 A | 8/1994 | Eden |
| 5,397,709 A | 3/1995 | Berndt |
| 5,501,959 A | 3/1996 | Lancaster et al. |
| 5,573,950 A | 11/1996 | Graessle et al. |
| 5,585,232 A | 12/1996 | Farr |
| 5,589,350 A | 12/1996 | Bochner |
| 5,627,045 A | * 5/1997 | Bochner ................... 435/34 |
| 5,681,737 A | 10/1997 | Gee et al. |
| 5,800,785 A | 9/1998 | Bochner |

(List continued on next page.)

FOREIGN PATENT DOCUMENTS

| | | |
|---|---|---|
| EP | 329120 | 2/1989 |
| EP | 0451775 | 1/1995 |
| WO | WO 82/02563 | 8/1982 |
| WO | WO 94/01528 | 1/1994 |
| WO | WO 94/19698 | 9/1994 |

OTHER PUBLICATIONS

Baughman et al., "Laboratory Capacity to Detect Antimicrobial Resistance," MMWR 48:1167–1171 [2000].

Bianchi and Baney, "Stress Responses as a Tool to Detect and Characterize the Mode of Action of Antibacterial Agents," Appl. Environ. Microbiol. 65:5023–5027 [1999].

Garland, "Analysis and interpretation of cummunity–level physiological profiles in microbial ecology," FEMS Microbiol. Ecol., 24:289–900 [1997].

(List continued on next page.)

*Primary Examiner*—Louise N. Leary
(74) *Attorney, Agent, or Firm*—Medlen & Carroll, LLP (57) ABSTRACT

The present invention relates to using multitest panels to improve the effectiveness, throughput, and efficiency of testing and commercial development of biologically active compounds, in particular those useful in human, animal, and plant health. In particular, the present invention provides phenotype microarrays suitable for testing biologically active compounds for their potential application in clinical, veterinary, and plant health.

24 Claims, 4 Drawing Sheets

| | phe 1 | phe 2 | phe 3 | phe 4 | phe 5 | phe 6 | phe 7 |
|---|---|---|---|---|---|---|---|
| NORMAL | + | + | + | + | + | + | + |
| MUTANT | – | + | + | + | + | + | + |
| NORMAL + DRUG 1 | – | + | + | + | + | + | + |
| NORMAL – DRUG 2 | – | + | + | + | – | + | + |

U.S. PATENT DOCUMENTS

| | | | |
|---|---|---|---|
| 5,811,231 A | 9/1998 | Farr | |
| 5,843,699 A | 12/1998 | Strenkoski et al. | |
| 5,882,882 A | 3/1999 | Bochner | |
| 5,888,760 A | 3/1999 | Godsey et al. | |
| 5,888,825 A | 3/1999 | Carr et al. | |
| 5,989,853 A | 11/1999 | Bochner et al. | |
| 6,046,021 A * | 4/2000 | Bochner | 435/34 |
| 6,103,479 A | 8/2000 | Taylor | 435/4 |

OTHER PUBLICATIONS

R. Hansen, University of Rochester; S.N. Wigging, Texas A&M University; J.A. Dimasi, Tufts University Office of Technology Assessment, in *Healthcare Marketplace Guide Research Reports 2000*, 15th edition, vol. 1, Dorland's Biomedical, Philadelphia, PA 19102, [1999–2000], at page I–172.

Harch et al., "Using the Gini coefficient with BIOLOG substrate utilisation data to provide an alternative quantitative measure for compiling bacterial soil communities," J. Microbiol. Meth., 30:91–101 [1997].

Hindler, "Antimicrobiol Susceptibility Testing," in Isenberg (ed.), *Clinical Microbiology Procedures Handbook*, vol. 1, American Society for Microbiology, Washington, D.C., [1994], pp. 5.0.1 through 5.25.1.

Jorgensen and Sahm, Antimicrobial Susceptibility Testing: General Considerations, in Murray et al., (eds.) *Manual of Clinical Microbiology*, 6th edition, American Society for Microbiology, Washington, D.C. [1995], pp. 1277–1280).

Khurshid et al., "*Staphylococcus aureus* with Reduced Susceptibility to Vancomycin," MMWR, 48:1165–1167 [2000].

Moir et al. "Genomics and Antimicrobial Drug Discovery," Antimicrob. Agents Chemother. 43:439–446 [1999].

Trias and Gordon, Curr. Opin. Biotechnol., 8:757–762 [1997].

U.S. patent application Ser. No. 09/267,039.

U.S. patent application Ser. No. 09/277,353.

Breithaupt, "Can novel antibacterial treatments combat the rising tide of drug–resistant infections?" Nature Biotech., 17:1165–1169 [1999].

Morrissey and Osbourn, "Fungal Resistance to Plant Antibiotics as a Mechanism of Pathogenesis," Microbiol. Mol. Biol. Rev., 63:708–774 [1999].

Pfaller et al., "Bacterial Pathogens Isolated from Patients with Bloodstream Infection: Frequencies of Occurrence and Antimicrobiol Susceptibility Patterns from the SENTRY Antimicrobial Surveillance Program (United States as Canada)," Antimicrob. Agents Chemother., 42:1762–1770 [1998].

Rieger et al., "Large–Scale Phenotypic Analysis—the Pilot Project on Yeast Chromosome III," Yeast 13:1547–1562 [1997].

Rieger et al., "Chemotyping of Yeast Mutants Using Robotics," Yeast 15:973–986 (1999).

Snydman et al., "Multicenter Study of In Vitro Susceptibility of the *Bacteroides fragilis* Group, 1995 to 1996, with Comparison of Resistance Trends from 1990 to 1996," Antimicrob. Agents Chemother., 43:2417–2422 [1999].

Steward et al., "Comparison of Agar Dilution, Disk Diffusion, MicroScan, and Vitek Antimicrobial Susceptibility Testing Methods to Broad Microdilution for Detection of Fluoroquinolone–Resistant Isolates of the Family Enterobacteriaceae," J. Clin. Microbiol., 37:544–547 [1999].

Thomas et al., "Pharmacodynamic Evaluation of Factors Associated with the Development of Bacterial Resistance in Acutely III Patients during Therapy," Antimicrob. Agents Chemother., 42:521–527 [1998].

Thornsberry et al., "Survey of Susceptibility of *Streptococcus pneumoniae, Haemophilus influenza*, and *Moraxella catarrhalis* Isolates 26 Antimicrobial Agents: a Prospective U.S. Study," Antimicrob. Agents Chemother., 43:2612–2623 [1999].

Coudron et al., "Tetrazolium Reduction as an Aid for Streptococcal Growth Detection with Agar Dilution Susceptibility Testing," J. Clin. Microbiol., 18: 765–769 (1983).

Bartlett and Mazens, "Rapid Antimicrobial Susceptibility Test Using Tetrazolium Reduction," Antimicrob. Agents Chemother. 15:769–777 (1979).

Kouda et al., "Bioluminescent Assay as a Potential Method of Rapid Susceptibility Testing," Microbiol. Immunol., 29:309–315 (1985).

Urban and Jarstrand, "Rapid determination of the susceptibility of bacteria to antibiotics with 'Sensitive' plates and nitroblue tetrazolium" J. Antimicrob. Chemother. 8:363–369 (1981).

Kroemer et al., "Mikrotitrierverfahren zur Bestimmung der antibiotischen Empfindlichkeit bei Staphylokokken mit Tetrazoliumsalzen," Use of a Microtiter–System for the Determination of the Antibiotic Susceptibility of a Staphylococci with Tetrazolium Salts, Zbl. Bdkt. Hyg. Abt. Orig., Λ 239: 42–45 (1977).

Chen et al., "Use of Molecular and Reference Susceptibility Testing Methods in a Multicenter Evaluation of MicroScan Dried Overnight Gram–Positive MIC Panels for Detection of Vancomycin and High–Level Aminoglycoside Resistances in Enterococci," J. Clin. Microbiol. 36:2996–3001 (1998).

Jorgensen et al., "Evaluation of the Dade MicroScan MICroSTREP Antimicrobial Susceptibility Testing Panel with Selected *Streptococcus pneumoniae* Challenge Strains and Recent Clinical Isolates," J. Clin. Microbiol., 36:788–791 (1998).

Hattori et al., "Novel Antibiotics Susceptibility Tests by the ATP–Bioluminescence Method Using Filamentous Cell Treatment", Antimicrob. Agents Chemother., 42:1406–1411 (1998).

Blondelle et al., "Mixture–Based Heterocyclic Combinatorial Positional Scanning Libraries: Discovery of Bicyclic Guanidines Having Potent Antifungal Activities Against *Candida albicans* and *Cryptococcus neoformans,*" Antimicrob. Agents Chemother., 43:106–114 (1999).

Silen et al., "Screening for Novel Antimicrobials from Encoded Combinatorial Libraries by Using a Two–Dimensional Agar Format," Antimicrob. Agents Chemother., 42:1447–1453 (1998).

Cockerill, "Genetic Methods for Assessing Antimicrobial Resistance," Antimicrob. Agents Chemother., 43:199–212 (1999).

Hong et al., "Identification and Characterization of Novel Antimicrobial Decapeptides Generated by Combinatorial Chemistry," Antimicrob. Agents Chemother., 42:2534–2541 (1998).

Ross–Macdonald et al., "Large–scale analysis of the yeast genome by transposon tagging and gene disruption," Nature 402:413–418 (1999).

Oliver et al., "Systematic functional analysis of the yeast genome," Tib–Tech 16:373–378 (1998).

Hampsey, "A Review of Phenotypes in *Saccharomyces cerevisae*," *Yeast* 13:1099–1133 (1997).

Seiler and Busse, "Identification of Yeasts with Microtiter Plates," *Forum Microbiologie* 11:505–509 (1988).

Seiler and Busse, "The Yeasts of Cheese Brines," *Intern. J. Food Microbiol.*, 11:289–304 (1990).

Seiler et al., "Identification of Moulds With Microtitration Plates," *Milchwissenschaft* 49:248–252 (1994).

Heard and Fleet, "A Convenient Microtitre Tray Procedure for Yeast Identification," *J. Appl. Bacteriol.*, 68:447–451 (1990).

Shelef et al., "Novel selective and non–selective optical detection of microorganisms," *Lett. Appl. Microbiol.*, 25: 202–206 (1997).

Abbott et al., "*Escherichia coli* O157:H7 Generates a Unique Biochemical Profile on MicroScan Conventional Gram–Negative Identification Panels," *J. Clin. Microbiol.*, 32: 823–824 (1994).

Miller et al., "Evaluation of Biolog for Identification of Members of the Family Micrococcaceae," *J. Clin. Microbiol.*, 31(12): 3170–3173 (1993).

Miller et al., "Evaluation of API An–IDENT and RapID ANA II Systems for Identification of Actinomyces Species from Clinical Specimens," *J. Clin. Microbiol.*, 33(2):329–330 (1995).

Williams et al., "Numerical Classification of Streptomyces and Related Genera," *J. Gen. Microbiol.*, 129:1743–1813 (1983).

Kampfer et al., "A numerical classification of the genera Streptomyces and Streptoverricillium using miniaturized physiological tests," *J. Gen. Microbiol.*, 137:1831–1891 (1991).

Kampfer and Kroppenstedt, "Probabillistic Identification of Streptomycetes Using Miniaturized Physiological Tests," *J. Gen. Microbiol.*, 137:1893–1902 (1991).

Farmer et al., "Biochemical Identification of New Species and Biogroups of Enterobacteriaceae Isolated from Clinical Specimens," *J. Clin. Microbiol.*, 21:46–76 (1985).

"Characteristics of GELRITE Gels," in GELRITE™—Gellan Gum Thermal–Reversible Gelling Agent, Commercial Development CD–26, Kelco, San Diego.

Blondelle et al., "Synthetic Combinatorial Libraries: Novel Discovery Strategy for Identification of Antimicrobial Agents," *Antimicrob. Agents Chemother.*, 40:1067–1071 (1996).

Kemp and Meredith, "Toxicity of Commercial Products on Cells in Suspension Culture: A Possible Screen for the Draize Eye Irritation Test," *Food Chem. Toxicol.*, 23:267–270 (1985).

Saint–Dizier et al., "The A.H.E.A.D. Method: A Quantitative Automated Measurement of the Hematotoxicity of Anticancer Drugs," *Anticancer Res.*, 10:765–772 (1990).

Walker and Ginsler, "Development of a Quantitative In Vitro Transformation Assay for Kidney Epithelial Cells," *Carcinogenesis* 13:25–32 (1992).

Loida et al., "Novel Inhibitors of Glutamyl–tRNA$^{Glu}$ Reductase Identified Through Cell–Based Screening of the Hemc/Chlorophyll Biosynthetic Pathway," *Arch. Biochem. Biophys.*, 372:230–237 (1999).

Henry, "Antibiotic Resistance: The Specter of Antibiotic Resistance has Roused Pharmaceutical and Biotechnology Companies to Seek New Weapons to Battle Infections," *Chem. Engineer. News*, Mar. 6, 2000, pp. 41–58.

Timmins, "Development of a High–Throughput Assay System for the Discovery of Anti–Bacterial Drugs," Abstract C–322, in American Society for Microbiology, Abstracts of the 100th General Meeting, May 24, 2000, p. 206.

Manome et al., Rapid Antimicrobial Susceptibility Testing Based on Menadione Mediated Chemiluminescence Assay,: Abstract C0320 In American Society for Microbiology, Abstracts of the 100th General Meeting, May 24, 2000, pp. 205–206.

Wun et al., "A New Procedure to Enhance fhuF Expression and Sidcrophore Production," Abstract I–134, in American Society for Microbiology, Abstracts of the 100th General Meeting, May 24, 2000, p. 411.

Nagar and Stitt, "A Method for Studying Viable but Non–Cultrable Organisms," Abstract I–136, in American Society for Mcirobiology Abstracts of the 100th General Meeting, May 24, 2000, p. 411.

Nagar and Stitt, "A Novel Method to Study Sublethally Injured Organisms," Abstract I–137, in American Society for Microbiology, Abstracts of the 100th General Meeting, May 24, 2000, p. 411.

Abstract for LRIG Meeting, Feb. 15, 2000.

Mullanc, "Cellular Assays to Drug Discovery," *Pharmaceut. Lab.* (Jun. 2000).

* cited by examiner

|  | phe 1 | phe 2 | phe 3 | phe 4 | phe 5 | phe 6 | phe 7 |
|---|---|---|---|---|---|---|---|
| NORMAL | + | + | + | + | + | + | + |
| MUTANT | − | + | + | + | + | + | + |
| NORMAL + DRUG 1 | − | + | + | + | + | + | + |
| NORMAL + DRUG 2 | − | + | + | + | − | + | + |

FIG. 1

|  | phe 1 | phe 2 | phe 3 | phe 4 | phe 5 | phe 6 | phe 7 |
|---|---|---|---|---|---|---|---|
| NORMAL | + | + | + | + | + | + | + |
| MUTANT | − | + | + | + | + | + | + |
| NORMAL + DRUG 1 | − | + | + | + | + | + | + |
| NORMAL + DRUG 2 | + | + | + | + | − | + | + |
| NORMAL + DRUG 1 & 2 | − | + | + | + | − | − | − |

COMPARATIVE PHENOTYPE ANALYSIS FOR ASSESSMENT OF BIOLOGICALLY ACTIVE COMPOUNDS SUCH AS ANTIMICROBIALS

This application is a continuation of U.S. patent application Ser. No. 09/556,898, filed Apr. 20, 2000.

FIELD OF THE INVENTION

The present invention relates to using multitest panels to improve the effectiveness, throughput, and efficiency of testing and commercial development of biologically active compounds, in particular those useful in human, animal, and plant health.

BACKGROUND OF THE INVENTION

Biologically active chemicals (BACs) constitute major, important commercial product lines. These compounds are generally focused toward enhancing the health of humans, other animals and plants. The largest markets are for drugs, especially antimicrobials and pharmaceuticals for human use. Because of the large market, major efforts and expenditures are made annually, in the pursuit of better and more effective BACs.

Antimicrobials constitute a major category of BACs. Although many antimicrobials have been developed and marketed, there remains a critical need for novel antimicrobials acting at novel targets. To some extent, this need is driven by the rapid emergence of antimicrobial-resistant pathogens. The appearance of strains resistant to all available drugs (e.g., enterococci), and the lag in the discovery of new antimicrobials has resulted in a renewed search for compounds effective against these resistant organisms. Despite this critical need and substantial research efforts, no new chemical entity has been approved by the U.S. Food and Drug Administration (FDA) for bacterial disease treatment for more than 20 years (Trias and Gordon, Curr. Opin. Biotechnol., 8:757–762 [1997]; See also, Bianchi and Baneyx, Appl. Environ. Microbiol., 65:5023–5027 [1999]).

The situation is particularly desperate in the area of nosocomial infections, as infections with methicillin-resistant *Staphylococcus aureus* (MRSA) and vancomycin-resistant *Enterococcus faecium* (VRE) have increased in frequency. There is a very real fear that high-level vancomycin resistance will spread within the staphylococci. Indeed, since 1996, vancomycin-intermediate *S. aureus* isolates (VISA; with vancomycin minimum inhibitory concentration [MIC] of 8–16 $\mu$g/ml), have been identified in Europe, Asia, and the U.S. This emergence of reduced vancomycin susceptibility in *S. aureus* increases the chances that some strains will become fully resistant, and currently used antimicrobials will become ineffective against such strains. This is of special concern because the emergence of community-acquired MRSA infections, has led to the increasing use of vancomycin against these organisms. Because very few therapies are available for treatment of MRSA, the confirmed reports of VISA strains demonstrating reduced susceptibility to vancomycin, the drug of last resort to treat MRSA, is of great concern (See e.g., Khurshid et al., MMWR, 48:1165–1167 [2000]; See also, Baughman et al., MMWR 48:1167–1171 [2000]).

Currently, the most commonly used antimicrobials are directed against a surprisingly small number of cellular functions as targets (e.g., cell wall, DNA, RNA, and protein biosynthesis). Table 1 summarizes these targets, gene products, and some antimicrobial classes that interact with the targets currently used. Instances of organism resistance to these antimicrobials are well-documented and widespread. Thus, it is clear that new antimicrobials are needed to counter the problem of increasing antimicrobial resistance.

The efforts to discover new, effective antimicrobials involve two steps. In the first step, one or more drug targets are defined. Targeting of new pathways beyond those shown in Table 1 will likely play an important role in this stage of development. In the second step, potentially active chemicals are screened and evaluated to find those that have the desired activity without engendering undesirable side effects.

TABLE 1

Targets of Some Widely Used Antimicrobials*

| Target Category and Gene Product | Antimicrobial Class |
| --- | --- |
| Protein Synthesis | |
| 30S Ribosomal Subunit | Aminoglycosides, Tetracyclines |
| 50S Ribosomal Subunit | Macrolides, Chloramphenicol |
| tRNA$^{ILE}$ Synthetase | Mupirocin |
| Elongation Factor G | Fusidic Acid |
| Nucleic Acid Synthesis | |
| DNA Gyrase A Subunit; Topoisomerase IV | Quinolones |
| DNA Gyrase B Subunit | Novobiocin |
| RNA Polymerase Beta Subunit | Rifampin |
| DNA | Metronidazole |
| Cell Wall Peptidoglycan Synthesis | |
| Transpeptidases | Beta-lactams |
| D-Ala-D-Ala Ligase Substrate | Glycopeptides |
| Antimetabolites | |
| Dihydrofolate Reductase | Trimethoprim |
| Dihydropteroate Synthesis | Sulfonamides |
| Fatty Acid Synthesis | Isoniazid |

*After, Moir et al., Antimicrob. Agents Chemother., 43:439–446 [1999]).

Another major category of BACs are pharmaceuticals (i.e., drugs) designed to counteract human diseases. Diseases can be viewed as abnormalities in physiological pathways of cells. The main components of these pathways are proteins (enzymes, receptors, etc.) encoded by genes and expressed within the cells affected by the disease. Drugs usually exert their pharmaceutical effect by interacting with key proteins (i.e., drug targets) to restore the normal functioning of the protein or to inactivate the protein and compensate for a physiological pathway abnormality.

As with antimicrobials, the process of developing pharmaceuticals involves two steps: (1) defining drug targets and then, (2) screening potential active chemicals to find the ones that specifically interact with the target to produce the desired effect without undesirable side effects. Although much work has been done in this area, there remains a need for improvements in the efficiency and effectiveness of the screening and evaluation of these chemicals.

In response to the pressures to generate more promising drugs, pharmaceutical and biotechnology companies have turned toward more rapid high-throughput methods to find and evaluate lead compounds. These lead compounds are typically selected by screening large libraries of compounds compiled from a wide variety of sources, using collections of extracts, chemicals synthesized by combinatorial chemistry approaches, or through rational drug design.

However, these methods have been a mixed blessing. Technologies such as combinatorial chemistry allow for rapid generation and screening of libraries of compounds against potential drug targets. Unfortunately, these technologies only look at the effect of the drugs on the proposed target, and they do not measure the effect on other cellular processes. A chemical may be an excellent candidate based on its interaction with the target protein, but it may also interact with other proteins in the cell and cause side effects. Thus, a major problem remains, in that the drug developer must sort through promising drug candidates to see how they effect other aspects of cell function, as well as how the drug candidates interact with other drugs that may be used simultaneously. Despite advances in these fields, there remains a need for highly sensitive and specific, yet cost-effective and easy-to-use methods for the identification and development of BACs that are effective in the treatment of disease.

SUMMARY OF THE INVENTION

The present invention relates to using multitest panels to improve the effectiveness, throughput, and efficiency of testing and commercial development of biologically active compounds, in particular those useful in human, animal, and plant health.

The present invention provides methods for testing the response of an organism to at least one biologically active chemical comprising the steps of: a) providing a testing device having at least two wells, wherein each well of the testing device contains at least one substrate selected from the group consisting of carbon sources, nitrogen sources, phosphorus sources, sulfur sources, growth stimulating nutrients, antimicrobials, and chromogenic testing substrates; and a suspension comprising an organism and at least one biologically active chemical; b) inoculating the suspension into the wells of the testing device; and c) observing the response of the organism to the biologically active chemical(s). In some embodiments, the testing device is selected from the group consisting of microtiter plates and microcards. In other embodiments, the suspension further comprises a gelling agent. In still other embodiments, the testing device further comprises a gel-initiating agent in said wells. In some preferred embodiments, the suspension further comprises a colorimetric indicator, while in other preferred embodiments the testing device further comprises a colorimetric indicator in the wells. In further embodiments, the observing is visual, while in other particularly preferred embodiments, the observing is performed by an instrument.

The present invention also provides methods for comparing the effect of at least two biologically active chemicals comprising the steps of: a) providing a first cell suspension comprising an organism and at least one biologically active chemical, a second cell suspension comprising the same organism as in the first cell suspension and at least one biologically active chemical, wherein the biologically active chemical is different from the biologically active chemical in the first cell suspension; a first testing device having wells, wherein the wells contain at least one substrate selected from the group consisting of carbon sources, nitrogen sources, phosphorus sources, sulfur sources, growth stimulating nutrients, antimicrobials, and chromogenic testing substrates; a second testing device having wells, wherein the wells contain at least one substrate selected from the group consisting of carbon sources, nitrogen sources, phosphorus sources, sulfur sources, growth stimulating nutrients, antimicrobials, and chromogenic testing substrates; b) adding the cell suspension to the wells of the first testing device to provide a first phenotype array; c) adding the cell suspension to the wells of the second testing device to provide a second phenotype array; d) incubating the first and second phenotype arrays; e) observing the response of the cell suspension in the first and the second phenotype arrays; and f) comparing the response of the cell suspension in the first phenotype array with the response of the cell suspension in the second phenotype array. In some embodiments, the first and second testing devices are selected from the group consisting of microtiter plates and microcards. In other embodiments, the first and second cell suspensions further comprise a gelling agent. In still other embodiments, the first and second testing devices further comprise a gel-initiating agent in the wells. In some preferred embodiments, the first and second cell suspensions further comprise a calorimetric indicator, while in other embodiments the first and second testing devices further comprise a colorimetric indicator in the wells. In some particularly preferred embodiments, the first testing device contains the same substrates as the second testing device. In some preferred embodiments, the observing is performed visually, while in alternative preferred embodiments, the observing is performed by an instrument. In particularly preferred embodiments, the comparison of the response is performed using multi-dimensional pattern analysis.

The present invention also provides multiwell kits for testing the effect of at least one biologically active chemical comprising: at least one testing device having at least two wells, wherein the wells contain at least one substrate selected from the group consisting of carbon sources, nitrogen sources, phosphorous sources, sulfur sources, growth stimulating nutrients, antimicrobials, and chromogenic substrates; and a cell suspension medium containing at least one biologically active chemical. In some embodiments, the testing device is selected from the group consisting of microtiter plates and microcards. In some preferred embodiments, the cell suspension medium comprises a gelling agent, while in other embodiments the testing device comprises a gel-initiating agent in said wells. In some embodiments, the cell suspension further comprises a calorimetric indicator, while in still other embodiments, the testing device further comprises a colorimetric indicator in the wells.

DESCRIPTION OF THE INVENTION

The present invention relates to using multitest panels, referred to herein as "phenotype microarrays," or "PMs," to improve the effectiveness, throughput, and efficiency of testing and commercial development of biologically active compounds (BACs), in particular those useful in human, animal, and plant health.

Although particularly preferred embodiments of the present invention involve BACs such as antimicrobials and other compounds commonly used to treat disease or disease symptoms, the present invention also encompasses a wide range of BACs, including but not limited to nutrients, hormones, growth stimulating compounds, nutritional supplements, vitamins, metabolism-modifying compounds, insecticides, rodenticides, fungicides, herbicides, algicides, etc. It is further intended that the present invention encompasses BACs from any source. Thus, the present invention provides means to assess BACs from any source as well as for any suitable application.

As indicated above, major problems are associated with traditional methods utilized in drug discovery and development. For example, a major problem remains, in that the drug developer must first sort through drug candidates to find the promising ones and then sort through the promising drug candidates to see how they effect other aspects of cell function, as well as how they interact with other drugs that may be used simultaneously. The present invention provides methods to test this efficiently and effectively, since PMs provide cost-effective and rapid, physiologically-based analyses of in vivo drug activity.

In addition to aiding the screening of chemical libraries in an efficient, high-throughput manner, the present invention also finds use in detailed toxicological analyses. For example, it is contemplated that in assays utilizing mammalian cells, a battery of cell lines representing various organs are used to assay multiple drug candidates in an easy-to-use, high-throughput, rapid, and cost-effective manner. Based on these results, compounds that initially look promising, but that in fact cause unacceptable side effects can be eliminated from consideration before the start of costly clinical trials.

Importantly, the present invention also provides methods for the analysis of drugs used in combination. The advantages of this embodiment include the ability to assess the likely interaction of multiple drugs in vivo. For example, in some cases, drug combinations exert harmful or antagonistic interactions, while in other cases, drug combinations act synergistically to provide additional benefit to the patient. Examples of the latter include combinations such as sulfa drugs with trimethoprim, and penicillins with β-lactamase inhibitors.

As cost is always a consideration in the development of drugs and treatment regimens, the present invention provides distinct advantages over presently used methods. The present invention represents a significant time and cost savings for the development of drugs. For example, current estimates indicate that it currently takes an average of 14.9 years to develop a drug from first synthesis to final Food and Drug Administration (FDA) approval (See, R. Hansen, University of Rochester; S. N. Wigging, Texas A&M University; J. A. Dimasi, Tufts University Office of Technology Assessment, in *Healthcare Marketplace Guide Research Reports* 2000, 15th edition, volume 1, Dorland's Biomedical, Philadelphia, Pa. 19102, [1999–2000], at page I-172). The cost of developing a single new drug has been reported to have grown from $54 million in 1976 to the current average of S359 million (Hansen supra). In addition, billions of dollars are wasted because approximately nine out of ten drugs fail during the course of clinical trials (Hansen, supra). The ability to efficiently identify and characterize new drug candidates, as well as eliminate unsatisfactory candidates early in the drug discovery process can save pharmaceutical companies billions of dollars on an annual basis.

The present invention also provides methods and compositions suitable for determining the mode of action of a BAC of interest. In this embodiment, the invention utilizes PMs in broad assays of various cell functions. This allows the determination of which functions are most sensitively altered by the BAC. For example, if a BAC is shown to inhibit cell wall synthesis (e.g., vancomycin), the level of synergy between this test BAC and other BACs that also inhibit cell wall synthesis (e.g., cephalosporins, penicillins, etc.) can be easily and efficiently evaluated. The present invention can be used to make quantitative and qualitative determination(s) regarding the type and level of synergy between the BACs. In another example, the activity of BACs that inhibit enzymatic activity involved in biosynthesis of an amino acid such as isoleucine (e.g., sulfometuron methyl) may be observed (i.e., expected to be toxic) on minimal medium phenotypes, and the effect specifically reversed in phenotype media containing branch chain amino acids.

The present invention also finds use in determinations of the type and number of BAC targets present in cells. Such determinations are significant, in that preferred BACs have specific modes of action and no side effects. Each potential new BAC must satisfy a number of criteria prior to its approval for use.

The choice of a target is an important early step in the development of new BACs. In general, a target should provide adequate selectivity and spectrum (i.e., an antimicrobial will be highly specific and/or highly selective against the microbe with respect to the human host, and also be active against the desired pathogen spectrum); a target should be essential for the growth or viability of pathogens (i.e., at least under conditions of infection); and the function of the target should be known, so that assays and high throughput screens, such as those of the present invention can be utilized. The present invention also provides means to determine and assess the selectivity and spectrum of BACs, as well as the functionality, and degree of importance of various targets.

In some embodiments of the present invention, the activity of the BAC is determined in such a manner that side effects, such as an interaction with multiple targets, are observed. For example, in one test BAC 1 is a specific drug that inhibits one target, protein 1. This is distinguished from BAC 2, which is found to be a non-specific drug, that inhibits protein 1, as well as protein 5. In the case where inhibition of protein 5 would be deleterious, this BAC would be determined to be unsuitable for use.

Figure 1:
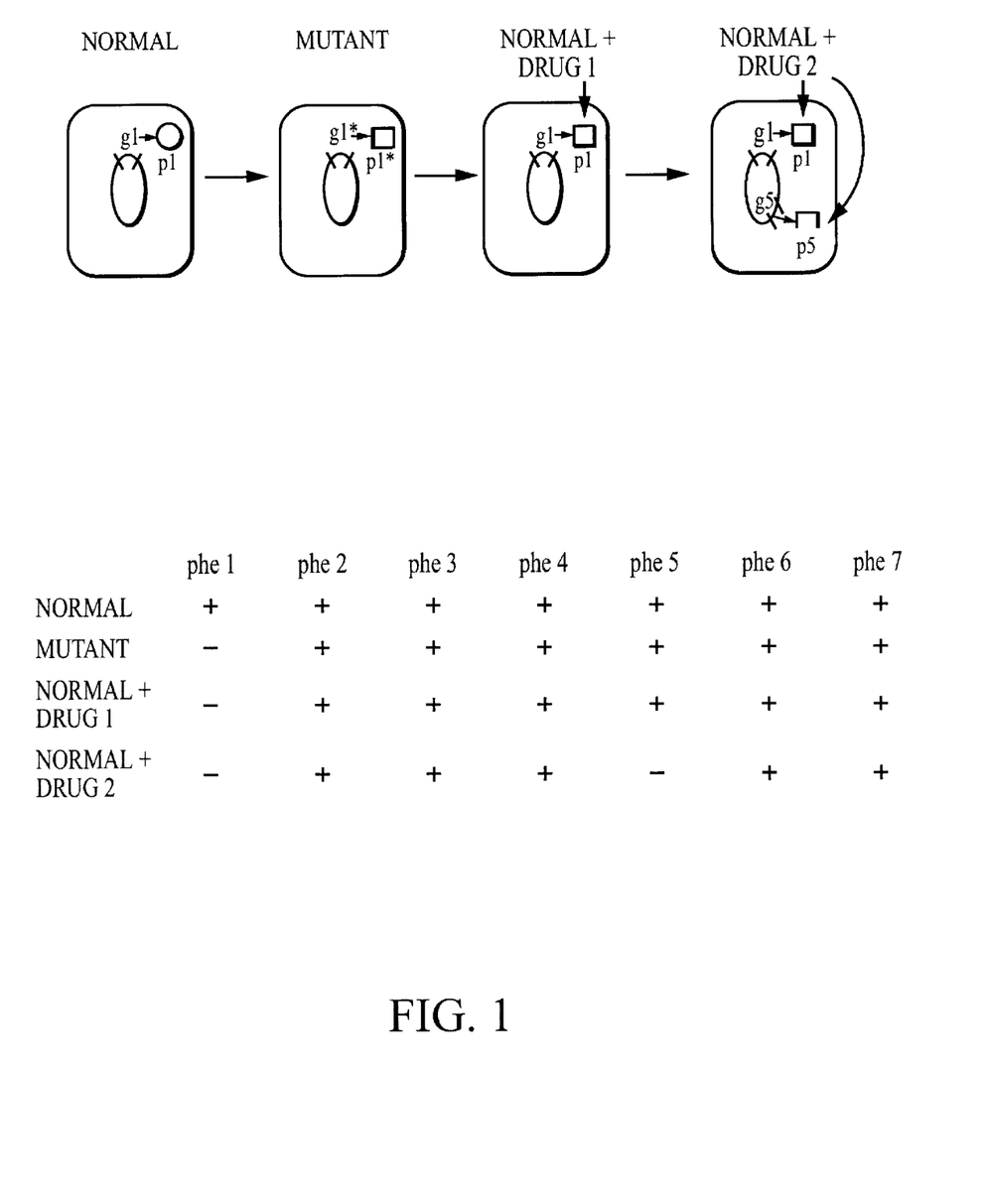
FIG. 1 provides a simple schematic of one embodiment of the present invention in which a drug target in a cell is inactivated by the addition of a drug to the cell. This testing is performed using PMs.
Figure 2:
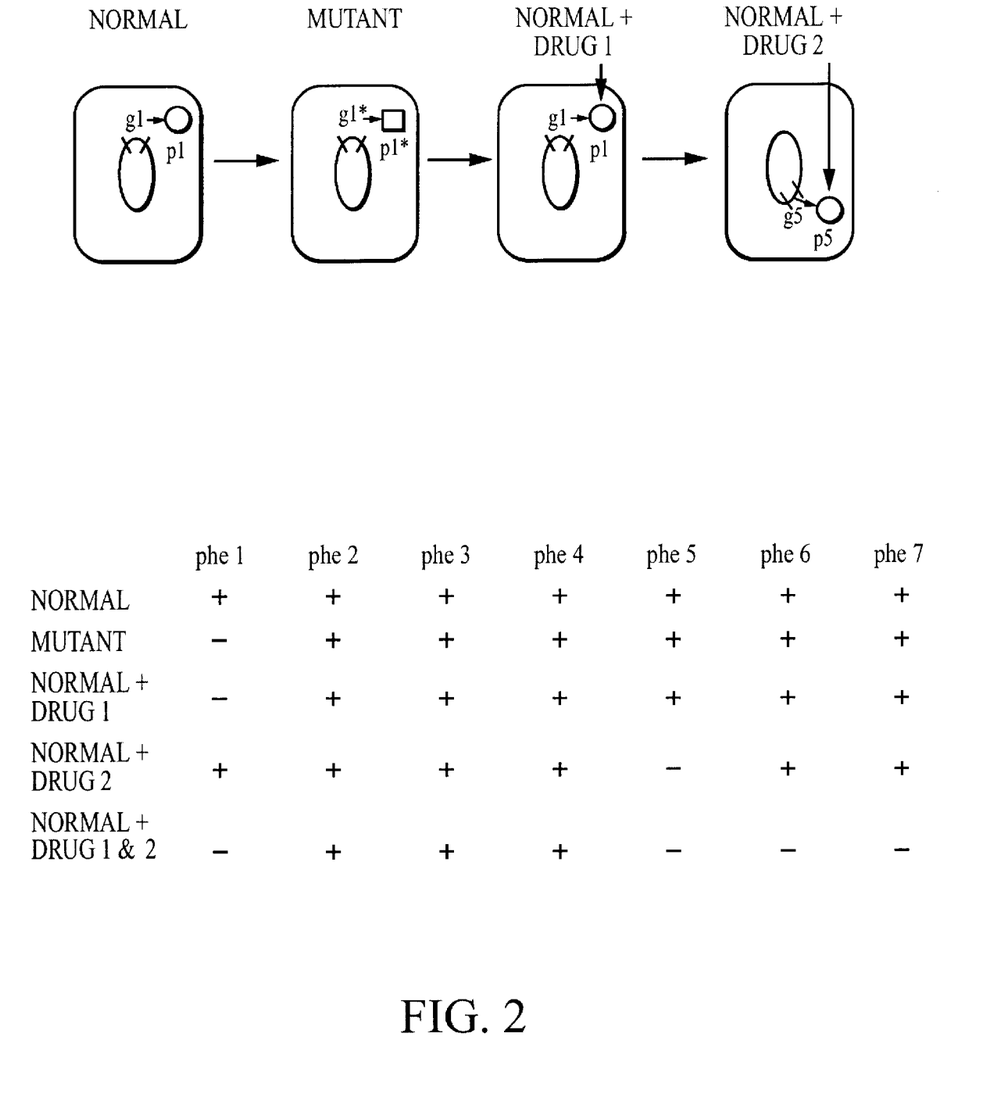
FIG. 2 provides a simple schematic of one embodiment of the present invention in which synergistic and antagonistic drug interactions are detected and characterized. This testing is also performed using PMs.

FIG. 1 provides a simplified schematic of one embodiment of the present invention designed to measure the effects of BACs on cells, using PMs. In this Figure and in FIG. 2, the "phe" designations indicate phenotypes of the cells (e.g., the growth and/or respiration of the cells in a particular well of the phenotype microarray). At the top left, FIGS. 1 and 2 show a normal cell and a mutant cell (e.g., a gene knockout) which lacks the functional activity of a normally encoded protein, which in this example, is a potential drug target. In FIGS. 1 and 2, "g1" indicates the gene that codes for protein "p1," which is the potential drug target. Most drugs work by blocking the activity of a protein, so when a drug is added, the cell now lacks the function of the target protein. Thus, in either case (i.e., the mutant cell or a normal cell exposed to a drug), the cell lacks the function of the target protein (e.g., p1). The major difference between these cells is that in the case of the mutant cell the protein function was eliminated by genetic means, whereas in the case of the normal cell exposed to the drug, the protein function was eliminated by chemical means. In FIG. 1, drug 1 is a good candidate for inactivating its target protein (p1), because it is active and specific (i.e., it only effects phenotype 1). In contrast, drug 2 is a poor candidate because it inactivates another protein, designated as protein 5 (p5), as well as p1 (i.e., it affects both phenotypes 1 and 5). Because drug 2 has non-specific effects on the cell, drug 2 is likely to cause side effects and be a less desirable compound to use in treatment regimens.

Thus, in some embodiments of the present invention, the activity of the BAC is determined in such a manner that side effects, such as an interaction with multiple targets, are observed. For example, in one test BAC 1 is a specific drug that inhibits one target, protein 1. This is distinguished from BAC 2, which is found to be a non-specific drug, that inhibits protein 1, as well as protein 5. In the case where inhibition of protein 5 would be deleterious, this BAC would be determined to be unsuitable for use.

FIG. 2 provides a simplified schematic of how PMs can detect drug interactions. When a cell is simultaneously exposed to "drug 1" and "drug 2," the consequent effect is more than just the effect of drug 1 (i.e., phe 1 changed) and drug 2 (i.e., phe 5 changed), as phe 6 and phe 7 were also changed. This demonstrates an extra effect of the drugs that cannot be predicted based on the known effects of the drugs used singly. These extra effects (i.e., changes on phe 6 and phe 7) may be beneficial (i.e., synergistic) or they may be harmful (i.e., antagonistic).

Figure 3:
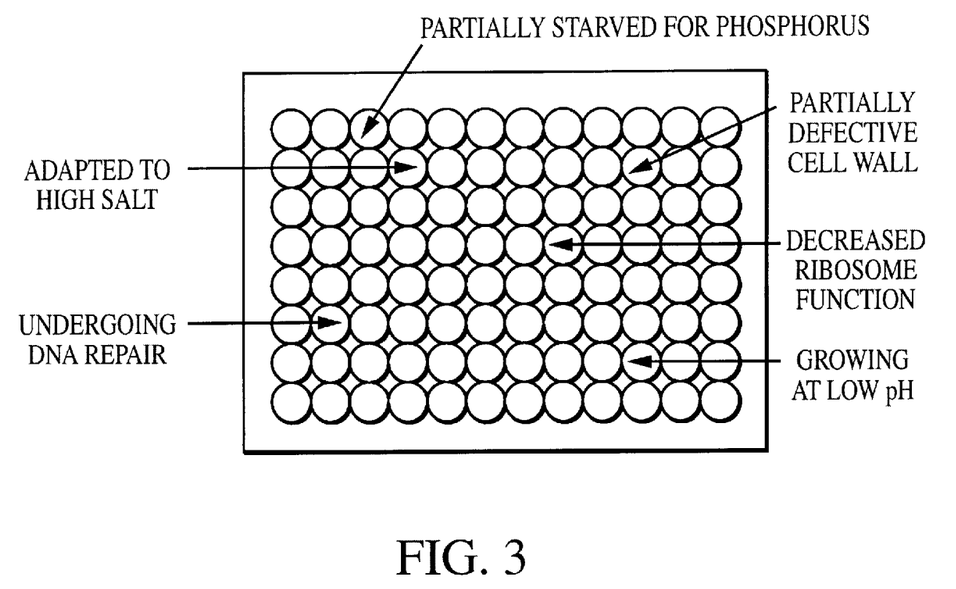
FIG. 3 provides a simplified schematic of the environmental conditions in various wells within a microtiter plate and the effect of these conditions on the cells within the wells.

As shown schematically in FIG. 3, during the testing process, the cells in various wells are placed under different environmental stresses. These stresses pressure the organisms to adapt in order to survive. For example, in some wells, the cells may be partially starved for an element such as phosphorus, while in other wells the cells may be adapting to high salt conditions, undergoing DNA repair, growing at low pH, producing partially defective cell walls, or experiencing decreased ribosome function. Thus, the present invention provides means, starting from a single culture (or cell population), to expose that culture to various environmental conditions, and thereby create an array of cells in different physiological states. If an antimicrobial drug or other BAC is also added to the culture, the present invention provides means to simultaneously observe the effect of the BAC on the culture under many environmental and physiological conditions. This is very different and much more powerful than current practice for such tasks as determining the antimicrobial susceptibility patterns of organisms, which typically grow the culture only under one condition that provides for rapid growth of the organism (i.e., optimal growth conditions).

In traditional and current methods for antimicrobial susceptibility testing, every effort is made to standardize the procedure and its interpretation. Although the methods are relatively simple (e.g., Kirby-Bauer disk diffusion and tube dilution methods), they are strictly controlled in the clinical setting by the National Committee for Clinical Laboratory Standards (NCCLS) (See, Hindler, "Antimicrobial Susceptibility Testing," in Isenberg (ed.), *Clinical Microbiology Procedures Handbook,* vol. 1, American Society for Microbiology, Washington, D.C., [1994], pages 5.0.1 through 5.25.1). Indeed, the practitioner is warned to not deviate from the standard methods or misleading results may be obtained.

However, although antimicrobial susceptibility tests are one of the most important tasks of the clinical microbiology laboratory, it is recognized that these tests simply provide an in vitro prediction of how well a particular antimicrobial will work to treat a patient's disease (See, Jorgensen and Sahm, "Antimicrobial Susceptibility Testing: General Considerations, in Murray et al., (eds.) *Manual of Clinical Microbiology,* 6th edition, American Society for Microbiology, Washington, D.C. [1995], pages 1277–1280). Because the approved testing procedures are highly standardized, there is no mechanism for testing the susceptibility of organisms under different environmental stresses. This is in direct contrast to the present invention, which allows the determination of antimicrobial susceptibility (as well as the determination of other characteristics of a particular culture) under multiple and widely different conditions, such as those that the organisms may encounter in vivo.

Thus, as indicated above, the present invention further finds use in the determination of synergy and antagonism. As is known in the art, it is important to know which BAC combinations are synergistic and which are antagonistic or harmful when utilized. The present invention provides methods and compositions for determining these relationships.

The results obtained using the present invention can produce simple or complex patterns which may be recorded quantitatively and analyzed using standard methods known in the art. In particular, multidimenstional pattern analysis methods, including but not limited to non-metric multidimensional scaling (NMDS), principle component and canonical variate analysis, heuristic clustering analysis, distance and similarity matrix generation, data extraction and mining activities, and bioinformatics tools and practices. In methods such as ANOVA, sample sets are compared based on how closely they have the same degree of variability. ANCOVA provides information about the joint variability of data sets. It is also contemplated that principle component analysis (PCA) and canonical variate analysis (CVA) will find use in the present invention. PCA provides an algebraic analysis of the data matrix, while CVA is applied to the distance or similarity matrix associated with the same algebraic analysis of the data. Correspondence analysis and discriminate analysis provide methods to use the basic PCA algorithm. As with CVA, the difference is how the data are handled prior to application of the algorithm. Monte Carlo permutation tests are also contemplated for use in conjunction with the present invention. These tests provide an indication of the stability and reliability of cluster analysis results.

In addition, it is contemplated that use of the Gini coefficient will be used in analyzing data obtained using the present invention (See e.g., Harch et al., J. Microbiol. Meth., 30:91–101 [1997]). For example, in this analysis, the Gini coefficient can be used as a measure to quantify unequal use of certain substrates or BACs. However, the choice of statistical methods well depend upon the use of the present invention. Thus, it is not intended that the present invention be limited to any particular method for data analysis. Indeed, it is contemplated that methods such as the Shannon index, as well as other suitable approaches will be used to analyze data generated using the present invention (See also, Garland, FEMS Microbiol. Ecol., 24:289–300 [1997]).

In addition, the present invention provides methods for determining data on BAC susceptibility profiles and permitting their easy storage in a database. In preferred embodiments, the present invention is suitable for the comparative phenotype testing of microorganisms as well as other cells.

In one preferred method, the present invention encompasses methods and compositions for the phenotypic testing of *E. coli* and *S. cerevisiae,* which are important prokaryotic and eukaryotic "model" organisms for many biological systems. However, it is not intended that the present invention be limited to these organisms. Indeed, it is contemplated that the present invention will find use in analyzing organisms of medical, veterinary, industrial, and environmental importance and/or interest.

It is not intended that the invention be limited to a particular genus, species nor group of organisms or cells. In addition to commonly isolated organisms, the range of cell types that can be tested using the methods and compositions of the present invention includes cells that undergo complex forms of differentiation, filamentation, sporulation, etc. Indeed, it is also intended that the present invention will find use with cells of any type, including, but not limited to cells maintained in cell culture, cell lines, etc., including mammalian, insect, and plant cells. The compositions and methods of the present invention are particularly targeted toward some of the most economically important organisms, as well as species of clinical importance. As various cells may be characterized using the PMs of the present invention, it is not intended that the choice of primary isolation or culture media be limited to particular formulae.

The present invention contemplates using a multiwell testing device essentially similar in structure to microtiter plates ("microplates" or "MicroPlates™" microtiter plates) which are commonly used in the art and commercially available from numerous scientific supply sources (e.g., Biolog, Fisher, etc.). It is also intended that the present invention encompasses various testing formats. Thus, in addition to standard microtiter plate testing methods, it is contemplated that the present invention be used with various gelling agents, including but not limited to alginate, carrageenan, and gellan gum (e.g., Gelrite™ and/or Phytagel™), as described in U.S. Pat. Nos. 5,627,045, and 5,882,882, and 5,989,853, as well as the MicroCard™ miniaturized testing plates described in U.S. Pat. Nos. 5,589,350 and 5,800,785 all of which are herein incorporated by reference.

Thus, in one embodiment, a microplate (e.g., a Micro-Plate™ microtiter plate) format is used. In this embodiment, the gel-forming matrix containing suspended cells is used to inoculate the wells of a MicroPlate™, MicroCard™ or another receptacle. At the time of inoculation, the gel-forming matrix is in liquid form, allowing for easy dispensing of the suspension into the compartments. These compartments contain dried biochemicals and cations. Upon contact of the gel-forming matrix with the cations, the suspension solidifies to form a soft gel, with the cells evenly distributed throughout. This gel is sufficiently viscous or rigid that to keep the cells suspended so that they do not sink to the bottom of the wells or testing array.

In another embodiment, a MicroCard™ miniaturized testing format is used. One embodiment of the device of the present invention comprises a housing with a liquid entry port through which the sample is introduced. The housing further contains a channel providing communication to a testing region so that a liquid can flow into a plurality of wells or compartments. The channel is enclosed by the surface of a hydrophobic, gas-venting membrane adapted for forming one surface of the wells and attached to one side of the housing. The housing can be sealed on its other side by a solid base. In other embodiments, a flexible tape may be substituted for the solid base or the solid base may be molded so as to be integral with the housing.

After filling the device with the solution or gel-forming matrix containing cells, an optional non-venting material such as tape (e.g., polyester tape) can be adhered to the outer surface of the gas-venting membrane to seal it against evaporation of the gel matrix within the device through the gas-venting membrane. At the time of delivery, the gel-forming matrix with suspended cells is in liquid form. Once the liquid comes into contact with gel-initiating compounds present in the testing region, a gel matrix is produced, trapping the suspended cells.

The present invention is particularly well-suited for use as a kit. In particular, this invention in the form of a kit, is suitable for the easy and rapid phenotypic testing of various cells, including commonly isolated bacteria, as well as actinomycetes and fungi (i.e., yeasts and molds), in addition to mammalian, insect, and plant cells. In particular, the present invention provides compositions and methods for the phenotypic analysis of cells, in particular, their susceptibility and resistance to various compounds with potential BAC activity.

While it is contemplated that the PMs of the present invention will be interpreted visually, it is also contemplated that instruments will find use in reading and interpreting the results of the assays. For example, a practical, efficient and cost-effective system for reading testing panels is described in U.S. patent application Ser. No. 09/277,353, which is hereby incorporated by reference. This instrument facilitates the direct and simultaneous analysis of cells and cell lines for thousands of phenotypes. The present invention provides methods and compositions for the phenotypic analysis of prokaryotic, as well as eukaryotic cells. Indeed, the present invention is not limited to any particular organism, cell, or testing format.

In many embodiments, the present invention provides one or more testing panels, with each test panel including substrates for 95 phenotypic tests. In particular, the present invention allows testing of numerous BAC compounds. However, it is not intended that the present invention be limited to a particular number of tests. For example, some panels are currently available that allow 384 or 1536 substrates to be tested in one array. Thus, the present invention allows testing of numerous BAC compounds. However, it is not intended that the present invention be limited solely to the testing of single BAC compounds. Thus, it is intended that the present invention encompasses testing panels with test substrates of any type suitable for the phenotypic testing of various cells. Indeed, it is contemplated that combinations of substrates will be used in the methods of the present invention, including individual BACs, potential BACs, combinations of BACs, and BACs tested in conjunction with other substrates (e.g., carbon or nitrogen sources).

Definitions

The terms "sample" and "specimen" in the present specification and claims are used in their broadest sense. On the one hand, they are meant to include a specimen or culture. On the other hand, they are meant to include both biological and environmental samples. These terms encompasses all types of samples obtained from humans and other animals, including but not limited to, body fluids such as urine, blood, fecal matter, cerebrospinal fluid (CSF), semen, and saliva, as well as solid tissue. These terms also refers to swabs and other sampling devices which are commonly used to obtain samples for culture of microorganisms.

Biological samples may be animal, including human, fluid or tissue, food products and ingredients such as dairy items, vegetables, meat and meat by-products, and waste. Environmental samples include environmental material such as surface matter, soil, water, and industrial samples, as well as samples obtained from food and dairy processing instruments, apparatus, equipment, disposable, and non-disposable items. These examples are not to be construed as limiting the sample types applicable to the present invention.

Whether biological or environmental, a sample suspected of containing microorganisms may (or may not) first be subjected to an enrichment means to create a "pure culture" of microorganisms. By "enrichment means" or "enrichment treatment," the present invention contemplates (i) conventional techniques for isolating a particular microorganism of interest away from other microorganisms by means of liquid, solid, semi-solid or any other culture medium and/or technique, and (ii) novel techniques for isolating particular microorganisms away from other microorganisms. It is not intended that the present invention be limited only to one enrichment step or type of enrichment means. For example, it is within the scope of the present invention, following subjecting a sample to a conventional enrichment means, to subject the resultant preparation to further purification such that a pure culture of a strain of a species of interest is produced. This pure culture may then be analyzed by the medium and method of the present invention.

As used herein, the term "primary isolation" refers to the process of culturing organisms directly from a sample. Thus, primary isolation involves such processes as inoculating an agar plate from a culture swab, urine sample, environmental sample, etc. Primary isolation may be accomplished using solid or semi-solid agar media, or in liquid. As used herein, the term "isolation" refers to any cultivation of organisms, whether it be primary isolation or any subsequent cultivation, including "passage" or "transfer" of stock cultures of organisms for maintenance and/or use.

As used herein, the term "culture" refers to any sample or specimen which is suspected of containing one or more microorganisms or cells. In particularly preferred embodiments, the term is used in reference to bacteria and fungi. "Pure cultures" are cultures in which the organisms present are only of one strain of a particular genus and species. This is in contrast to "mixed cultures," which are cultures in which more than one genus and/or species of microorganism are present.

As used herein, the term "organism" is used to refer to any species or type of microorganism, including but not limited to bacteria, yeasts and other fungi. As used herein, the term fungi, is used in reference to eukaryotic organisms such as the molds and yeasts, including dimorphic fungi.

As used herein, the term "spore" refers to any form of reproductive elements produced asexually (e.g., conidia) or sexually by such organisms as bacteria, fungi, algae, protozoa, etc. It is also used in reference to structures within microorganisms such as members of the genus Bacillus, which provide advantages to the individual cells in terms of survival under harsh environmental conditions. It is not intended that the term be limited to any particular type or location of spores, such as "endospores" or "exospores." Rather, the term is used in the very broadest sense.

As used herein, the terms "microbiological media" and "microbiological culture media," and "media" refer to any substrate for the growth and reproduction of microorganisms. "Media" may be used in reference to solid plated media which support the growth of microorganisms. Also included within this definition are semi-solid and liquid microbial growth systems including those that incorporate living host organisms, as well as any type of media.

As used herein, the terms "culture media," and "cell culture media," refers to media that are suitable to support the growth of cells in vitro (i.e., cell cultures). It is not intended that the term be limited to any particular cell culture medium. For example, it is intended that the definition encompass outgrowth as well as maintenance media. Indeed, it is intended that the term encompass any culture medium suitable for the growth of the cell cultures of interest.

As used herein, the term "cell type," refers to any cell, regardless of its source or characteristics.

As used herein, the term "cell line," refers to cells that are cultured in vitro, including primary cell lines, finite cell lines, continuous cell lines, and transformed cell lines.

As used herein, the terms "primary cell culture," and "primary culture," refer to cell cultures that have been directly obtained from animal, plant or insect tissue. These cultures may be derived from adults as well as fetal tissue.

As used herein, the term "finite cell lines," refer to cell cultures that are capable of a limited number of population doublings prior to senescence.

As used herein, the term "continuous cell lines," refer to cell cultures that have undergone a "crisis" phase during which a population of cells in a primary or finite cell line apparently ceases to grow, but yet a population of cells emerges with the general characteristics of a reduced cell size, higher growth rate, higher cloning efficiency, increased tumorigenicity, and a variable chromosomal complement. These cells often result from spontaneous transformation in vitro. These cells have an indefinite lifespan.

As used herein, the term "transformed cell lines," refers to cell cultures that have been transformed into continuous cell lines with the characteristics as described above. Transformed cell lines can be derived directly from tumor tissue and also by in vitro transformation of cells with whole virus (e.g., SV40 or EBV), or DNA fragments derived from a transforming virus using vector systems.

As used herein, the term "mixed cell culture," refers to a mixture of two types of cells. In some embodiments, the cells are cell lines that are not genetically engineered, while in other preferred embodiments the cells are genetically engineered cell lines.

As used herein, the term "auxotroph" is used in reference to an organism or cell line that can be grown only in the presence of nutritional supplements (e.g., growth factors). Thus, in auxotrophic testing, auxotrophs will only grow in the presence of the supplement(s) that is/are necessary for their growth, and will not grow in media that lack the necessary supplement(s).

As used herein, the term "carbon source" is used in reference to any compound which may be utilized as a source of carbon for cell growth and/or metabolism. Carbon sources may be in various forms, including, but not limited to polymers, carbohydrates, acids, alcohols, aldehydes, ketones, amino acids, and peptides.

As used herein, the term "nitrogen source" is used in reference to any compound which may be utilized as a source of nitrogen for cell growth and/or metabolism. As with carbon sources, nitrogen sources may be in various forms, such as free nitrogen, as well as compounds which contain nitrogen, including but not limited to amino acids, peptones, vitamins, and nitrogenous salts.

As used herein, the term "phosphorus source" is used in reference to any compound which may be utilized as a source of phosphorus for cell growth and/or metabolism. As with sources of other elements (e.g., carbon and nitrogen), phosphorus sources may be in various forms, such as free phosphorus, as well as compounds which contain phosphorus.

As used herein, the term "sulfur source" is used in reference to any compound which may be utilized as a source of sulfur for cell growth and/or metabolism. As with carbon, nitrogen and phosphorus sources, sulfur sources may be in various forms, such as free sulfur, as well as compounds which contain sulfur.

As used herein, the term "growth stimulating nutrients" is used in reference to any compounds that enhance the growth of an organism. It is not intended that the present invention be limited to any particular growth stimulating nutrients, although in particularly preferred embodiments, the present invention contemplates the use of growth factors, amino acids, nucleic acid precursors, lipids, cell membrane and wall precursors, vitamins, hormones, minerals, as well as other elements and compounds that stimulate growth of cells.

As used herein, the term "antimicrobial" is used in reference to any compound which inhibits the growth of, or kills microorganisms. It is intended that the term be used in its broadest sense, and includes, but is not limited to compounds such as antibiotics which are produced naturally or synthetically. It is also intended that the term includes any other organic and inorganic compounds that are useful for inhibiting the growth of, or killing microorganisms.

As used herein, the term "testing substrate" is used in reference to any nutrient source (e.g., carbon, nitrogen, phosphorus, and sulfur sources, as well as growth stimulating nutrients, antimicrobials, and chromogenic substrates) that may be utilized to differentiate bacteria based on biochemical characteristics. For example, one cell species may utilize one testing substrate that is not utilized by another species. This utilization may then be used to differentiate between these two species. It is contemplated that numerous testing substrates be utilized in combination. Testing substrates may be tested individually (e.g., one substrate per testing well or compartment, or testing area) or in combination (e.g., multiple testing substrates mixed together and provided as a "cocktail").

As used herein, the term "BAC" is used in reference to any compound that has an effect on a cell. The effect can be to stimulate or inhibit cell growth or respiration, to bind to any cellular component, to influence the activity of any function or protein-catalyzed activity of a cell. Thus, it is not intended that the present invention be limited to any compound or class of compounds. Indeed, the BACs of the present invention include any compound that has any effect on a particular cell.

Following exposure to a testing substrate (e.g., BAC(s), carbon or nitrogen sources, etc.), the response of an organism or cell line may be detected. This detection may be visual (i.e., by eye) or accomplished with the assistance of machine(s) (e.g., the Biolog MicroStation Reader™). For example, the response of organisms to carbon sources may be detected as turbidity in the suspension due to the utilization of the testing substrate by the organisms. Likewise, growth can be used as an indicator that an organism is not inhibited by certain BACs. In one embodiment, color is used to indicate the presence or absence of organism growth/metabolism.

As used herein, the term "calorimetric indicator" refers to any compound that is used to indicate by means of a color change that a reaction has occurred or that a cell or organism is capable of metabolizing a particular compound. This includes, but is not limited to any color, as used in the traditional sense of "colors," such as indigo, blue, red, yellow, green, orange, brow, etc., as well as fluorochromic or fluorogenic compounds, which produce colors detectable with fluorescence (e.g., the yellow-green of fluorescein, the red of rhodamine, etc.). It is intended that such other indicators as dyes (e.g., pH and redox) and luminogenic compounds be encompassed within this definition. In preferred embodiments, the calorimetric indicators of the present invention include, but are not limited to chromogenic substrates, oxidation-reduction indicators, and pH indicators. In some particularly preferred embodiments, the oxidation-reduction indicator is tetrazolium violet, while in other embodiments, the oxidation-reduction indicator is redox purple. The colorimetric indicator can be monitored visually or by means of a device or machine (e.g., a colorimeter, photometer or camera).

As used herein, the terms "chromogenic compound" and "chromogenic substrate," refer to any compound useful in detection systems by their light absorption or emission characteristics. The term is intended to encompass any enzymatic cleavage products, soluble, as well as insoluble, which are detectable either visually or with optical machinery. Included within the designation "chromogenic" are all enzymatic substrates which produce an end product which is detectable as a color change. This includes, but is not limited to any color, as used in the traditional sense of "colors," such as indigo, blue, red, yellow, green, orange, brown, etc., as well as fluorochromic or fluorogenic compounds, which produce colors detectable with fluorescence (e.g., the yellow-green of fluorescein, the red of rhodamine, etc.). It is intended that such other indicators as dyes (e.g., pH and redox) and luminogenic compounds be encompassed within this definition.

As used herein, the commonly used meaning of the terms "pH indicator," "redox indicator," and "oxidation-reduction indicator," are intended. Thus, "pH indicator" encompasses all compounds commonly used for detection of pH changes, including, but not limited to phenol red, neutral red, bromthymol blue, bromcresol purple, bromeresol green, bromchlorophenol blue, m-cresol purple, thymol blue, bromcresol purple, xylenol blue, methyl red, methyl orange, and cresol red. The terms "redox indicator" and "oxidation-reduction indicator" encompass all compounds commonly used for detection of oxidation/reduction potentials (i.e., "eH") including, but not limited to various types or forms of tetrazolium, resazurin, methylene blue, and quinone-imide redox dyes including the compounds known as "methyl purple" and derivatives of methyl purple. The quinone-imide redox dye known as methyl purple is referred to herein as "redox purple" (See e.g., U.S. Pat. No. 5,882,882, herein incorporated by reference). In a particularly preferred embodiment, "redox purple" comprises the compound with the chemical structure shown in FIG. 5, VI of U.S. Pat. No. 5,882,882. It is contemplated that analogous derivatives of the reagent (e.g., alkali salts, alkyl O-esters), with modified properties (e.g., solubility, cell permeability, toxicity, and/or modified color(s)/absorption wavelengths) will be produced using slight modifications of the methods described in the accompanying Examples. It is also contemplated that various forms of "redox purple" (e.g., salts, etc.), may be effectively used in combination as a redox indicator in the present invention.

As used herein, the terms "testing means" and "testing device" are used in reference to testing systems in which at least one organism is tested for at least one characteristic, such as utilization of a particular carbon source, nitrogen source, or chromogenic substrate, and/or susceptibility to a BAC agent. This definition is intended to encompass any suitable means to contain a reaction mixture, suspension, or test. It is intended that the term encompass microplates, petri plates, microcard devices, or any other supporting structure that is suitable of use. For example, a microplate having at least one gel-initiating agent included in each of a plurality of wells or compartments, comprises a testing means. Other examples of testing means include microplates without gel-initiating means included in the well. It is also intended that other compounds such as carbon sources or BACs will be included within the compartments. The definition encompasses the MicroPlate™ microtiter plates for characterization of microorganisms (available from Biolog). The definition is also intended to encompass a "microcard" or miniaturized plates or cards which are similar in function, but much smaller than standard microtiter plates (for example, many testing devices can be conveniently held in a user's hand). In particularly preferred embodiments, the microcards are the MicroCard™ device described in U.S. Pat. Nos. 5,589,350, and 5,800,785, both of which are herein incorporated by reference (available from Biolog). It is not intended that the present invention be limited to a particular size or configuration of testing device or testing means. For example, it is contemplated that various formats will be used with the present invention, including, but not limited to microtiter plates (includg but not limited to MicroPlates™), miniaturized testing plates (e.g., MicroCard™ miniaturized testing cards), petri plates, petri plates with internal dividers used to separate different media placed within the plate, test tubes, as well as many other formats.

As used herein, the term "gelling agent" is used in a broad generic sense, and includes compounds that are obtained from natural sources, as well as those that are prepared synthetically. As used herein, the term refers to any substance which becomes at least partially solidified when certain conditions are met. For example, one gelling agent encompassed within this definition is Gelrite™, a gellan which forms a gel upon exposure to divalent cations (e.g., $Mg^{2+}$ or $Ca^{2+}$); Gehite™ is a gellan gum, produced by deacetylating a natural polysaccharide produced by *Pseudomonas elodea*, and is described by Kang et al. (U.S. Pat. Nos. 4,326,052 and 4,326,053, herein incorporated by reference).

Included within the definition are various gelling agents obtained from natural sources, including protein-based as well as carbohydrate-based gelling agents. One example is bacteriological agar, a polysaccharide complex extracted from kelp. Also included within the definition are such compounds as gelatins (e.g., water-soluble mixtures of high molecular weight proteins obtained from collagen), pectin (e.g., polysaccharides obtained from plants), carrageenans and alginic acids (e.g., polysaccharides obtained from seaweed), and gums (e.g., mucilaginous excretions from some plants and bacteria). It is contemplated that various carrageenan preparations will be used in the present invention, with iota carrageenan comprising a preferred embodiment. It is also contemplated that gelling agents used in the present invention may be obtained commercially from a supply company, such as Difco, BBL, Oxoid, Marcor, Sigma, or any other source.

It is not intended that the term "gelling agent" be limited to compounds which result in the formation of a hard gel substance. A spectrum is contemplated, ranging from merely a more thickened or viscous colloidal suspension to one that is a firm gel. It is also not intended that the present invention be limited to the time it takes for the suspension to gel.

Importantly, it is intended that the present invention provides a gelling agent suitable for production of a matrix in which organisms may grow (i.e., a "gel matrix"). The gel matrix of the present invention is a colloidal-type suspension of organisms produced when organisms are mixed with an aqueous solution containing a gelling agent, and this suspension is exposed to a gel-initiating agent. It is intended that this colloidal-type gel suspension be a continuous matrix medium throughout which organisms may be evenly dispersed without settling out of the matrix due to the influence of gravity. The gel matrix supports the growth of organisms within, under, and on top of the gel suspension.

As used herein the term "gel-initiating agent" refers to any compound or element which results in the formation of a gel matrix, following exposure of a gelling agent to certain conditions or reagents. It is intended that "gel-initiating agent" encompass such reagents as cations (e.g., $Ca^{2+}$, $Mg^{2+}$, and $K^+$). Until the gelling agent contacts at least one gel-initiating agent, any suspension containing the gelling agent remains "ungelled" (i.e., there is no thickening, increased viscosity, nor hardening of the suspension). After contact, the suspension will become more viscous and may or may not form a rigid gel (i.e., contact will produce "gelling").

As used herein, the term "inoculating suspension" or "inoculant" is used in reference to a suspension which may be inoculated with organisms to be tested. It is not intended that the term "inoculating suspension" be limited to a particular fluid or liquid substance. For example, inoculating suspensions may be comprised of water, saline, or an aqueous solution which includes at least one gelling agent. It is also contemplated that an inoculating suspension may include a component to which water, saline or any aqueous material is added. It is contemplated in one embodiment, that the component comprises at least one component useful for the intended microorganism. It is not intended that the present invention be limited to a particular component.

As used herein, the term "kit" is used in reference to a combination of reagents and other materials. It is contemplated that the kit may include reagents such as BACs, carbon sources, nitrogen sources, chromogenic substrates, diluents and other aqueous solutions, as well as specialized microplates (e.g., GN, GP, ES, YT, SF-N, SF-P, and other MicroPlates™, obtained from Biolog), inoculants, miniaturized testing cards (e.g., MicroCards™), and plated agar media. The present invention contemplates other reagents useful for the growth, identification and/or determination of the BAC susceptibility of microorganisms. For example, the kit may include reagents for detecting the growth of microorganisms following inoculation of kit components (e.g., tetrazolium or resazurin included in some embodiments of the present invention). It is not intended that the term "kit" be limited to a particular combination of reagents and/or other materials. Further, in contrast to methods and kits which involve inoculating organisms on or into a preformed matrix such as an agar surface or broth, the present invention involves inoculation of a testing plate in which the organisms are suspended within a gel-forming matrix.

Although embodiments have been described with some particularity, many modifications and variations of the preferred embodiment are possible without deviating from the invention.

Experimental

The following examples are provided in order to demonstrate and further illustrate certain preferred embodiments and aspects of the present invention and are not to be construed as limiting the scope thereof.

In the experimental disclosure which follows, the following abbreviations apply: eq (equivalents); M (Molar); $\mu$M (micromolar); N (Normal); mol (moles); mmol (millimoles); $\mu$mol (micromoles); nmol (nanomoles); g (grams); mg (milligrams); $\mu$g (micrograms); ng (nanograms); l or L (liters); mi (milliliters); $\mu$l (microliters); cm (centimeters); mm (millimeters); pm (micrometers); nm (nanometers); ° C.

(degrees Centigrade); TSA (trypticase soy agar); YME or YEME (Yeast extract-malt extract agar); Redigel (RCR Scientific, Goshen, Ind.); Gelrite™ (Merck and Co., Rahway, N.J.); Remel, (Remel, Lenexa, Kans.); Oxoid (Oxoid, Basingstoke, England); BBL (Becton Dickinson Microbiology Systems, Cockeysville, Md.); DIFCO (Difco Laboratories, Detroit, Mich., now part of Becton-Dickinson); Acumedia (Acumedia, Baltimore, Md.); U.S. Biochemical (U.S. Biochemical Corp., Cleveland, Ohio); Fisher (Fisher Scientific, Pittsburgh, Pa.); Sigma (Sigma Chemical Co., St. Louis, Mo.); Biolog (Biolog, Inc., Hayward, Calif.); ATCC (American Type Culture Collection, Rockville, Md.); NCYC (National Collection of Yeast Cultures, Norwich, England); NCCLS (National Committee for Clinical Laboratory Standards); and Molecular Devices (Molecular Devices, Mountain View, Calif.). The three-letter abbreviations conventionally used for amino acids (e.g., "ala" designates alanine or an alanine residue) are also used in some of the following Examples.

EXAMPLE 1

BAC Testing of Bacteria

In this Example, the susceptibility of E. coli (MG1655) was tested in the presence of vancomycin (10 µg/ml) or sulfamethoxazole (235 µg/ml) in microarrays containing various additional compounds. The microarrays were present in three Biolog™ sensitivity test panels, referred to as ES1, ES2 and ES3 MicroPlates™. The organisms were added to a sterile aqueous suspension containing 0.40% NaCl, 0.03% pluronic F68, 0.01% phytagel, and 0.01% tetrazolium violet, to a cell density of 85% transmittance (as measured using a BiologTm turbidimeter). The BAC to be tested was added to the suspension just prior to inoculating the organisms (100 µl/well) into the wells of the microarrays. The wells of these ES MicroPlates™ contained a basal broth medium consisting of tryptone (2 g/L), yeast extract (1 g/L), and NaCl (1 g/L).

In addition to one positive control well, the wells of the ES 1 plates contained the following antimicrobials (one compound at a particular concentration per well): acriflavine (4.0 µg/ml, 8.0 µg/ml, and 16 µg/ml), ampicillin (2.0 µg/ml, 4.0 µg/ml, 8.0 µg/ml, and 16 µg/ml), nafcillin (75 µg/ml, 150 µg/ml, 300 µg/ml, and 600 µg/ml,), lincomycin (50 µg/ml, 100 µg/ml, 200 µg/ml, and 400 µg/ml), chloramphenicol (0.1 µg/ml, 0.2 µg/ml, 0.4 µg/ml, and 0.8 µg/ml), chlortetracycline (0.125 µg/ml, 0.25 µg/ml, 0.50 µg/ml, and 1.0 µg/ml), tetracycline (0.033 µg/ml, 0.066 µg/ml, 0.133 µg/ml, and 0.266 µg/ml), gentamycin (0.25 µg/ml, 0.50 µg/ml, 1.0 ,µg/ml, and 2.0 µg/ml), kanamycin (0.25 µg/ml, 0.5 µg/ml, 1.0 µg/ml, and 2.0 µg/ml), neomycin (0.75 µg/ml, 1.5 µg/ml, 3.0 µg/ml, and 6.0 µg/ml), vancomycin (10 µg/ml, 20 µg/ml, 40 µg/ml, and 80 µ/ml), bacitracin (208 µg/ml, 416 µg/ml, 833 µg/ml, and 1666 µg/ml), clindamycin (3.3 µg/ml, 6.6 µg/ml, 13.2 µg/ml, and 26.4 µg/ml), cloxacillin (100 µg/ml, 200 µg/ml, 400 µg/ml, and 800 µg/ml), erythromycin (2.5 µg/ml, 5.0 µg/ml, 10 µg/ml, and 20 µg/ml), penicillin G (5 µg/ml, 10 µg/ml, 20 µg/ml, and 40 µg/ml), novobiocin (33 µg/ml, 66 µg/ml, 133 µg/ml, and 266 µg/ml), spiramycin (5.0 µg/ml, 10 µg/ml, 20 µg/ml, and 40 µg/ml,), trimethoprim (0.17 µg/ml, 0.33 µg/ml, 0.67 µg/ml, and 1.3 µg/ml), streptomycin (0.38 µg/ml, 0.75 µg/ml, 1.5 µg/ml, and 3.0 µg/ml), cephaloridine (0.75 µg/ml, 1.5 µg/ml, 3.0 µg/ml, and 6.0 µg/ml), cefuroxime (0.5 µg/ml, 1.0 µg/ml, 2.0 µg/ml, and 4.0 µg/ml), roxithromycin (10 µg/ml, 20 µg/ml, 40 µg/ml, and 80 µg/ml), and piperacillin (0.5 µg/ml, 1.0 µg/ml, 2.0 µg/ml, and 4.0 µg/ml).

The wells of the ES2 plates contained the following antimicrobials (one compound at a particular concentration per well): azomycin (0.2 µg/ml, 0.4 µg/ml, 0.8 µg/ml, and 1.6 µg/ml), rifampicin (0.25 µg/ml, 0.5 µg/ml, 1.0 µg/ml, and 2.0 µg/ml), tylosin tartrate (25 µg/ml, 50 µg/ml, 100 µg/ml, and 200 µg/ml), cefazolin (0.5 µg/ml, 1.0 µg/ml, 2.0 µg/ml, and 4.0 µg/ml), cephalothin (2.5 µg/ml, 5.0 µg/ml, 10 µg/ml, and 20 µg/ml), cefaclor (0.66 µg/ml, 1.33 µg/ml,, 2.66 µg/ml, and 5.33 µg/ml), rifamycin SV (1.5 µg/ml, 3.0 µg/ml, 6.0 µg/ml, and 12 µg/ml), cefsulodin 4.0 µg/ml, 8.0 µg/ml, 16 µg/ml, and 32 µg/ml), cefotaxime (0.05 µg/ml, 0.1 µg/ml, 0.2 µg/ml, and 0.4 µg/ml), cefoxitin (0.75 µg/ml, 1.5 µg/ml, 3.0 µg/ml, and 6.0 µg/ml), puromycin (12 µg/ml, 25 µg/ml, 50 µg/ml, and 100 µg/ml), spectinomycin (3.5 µg/ml, 7.0 µg/ml, 14 µg/ml, and 28 µg/ml), fusidic acid (50 µg/ml, 100 µg/ml, 200 µg/ml, and 400 µg/ml), phosphomycin (0.2 µg/ml, 0.4 µg/ml, 0.8 µg/ml, and 1.6 µg/ml), phleomycin (0.25 µg/ml, 0.5 µg/ml, 1.0 µg/ml, and 2.0 µg/ml), amikacin (0.25 µg/ml, 0.5 µg/ml, 1.0 µg/ml, and 2.0 µg/ml), isoniazid (300 µg/ml, 600 µg/ml, 1200 µg/ml, 2400 µg/ml), ethionamide (25 µg/ml, 50 µg/ml, 100 µg/ml, and 200 µg/ml), SDS (50 µg/ml, 100 µg/ml, 200 µg/ml, 400 µg/ml), dodecyltrimethyl ammonium bromide (10 µg/ml, 20 µg/ml, 40 µg/ml, and 80 µg/ml), BIGCHAP (2000 µg/ml, 4000 µg/ml, 8000 µg/ml, and 16,000 µg/ml), niaproof (0.08%, 0.16%, 0.32%, and 0.64%), CHAPS (1500 µg/ml, 3000 µg/ml, 6000 µg/ml, 12,000 µg/ml), and N-lauryl sarcosine (1000 µg/ml, 2000 µg/ml, 4000 µg/ml and 8000 µg/ml).

The wells of the ES3 plates contained the following antimicrobials (one compound at a particular concentration per well): nalidixic acid (0.5 µg/ml, 1.0 µg/ml, 2.0 µg/ml, 4.0 µg/ml), taurocholic acid (600 µg/ml, 1200 µg/ml, 2400 µg/ml, and 4800 µg/ml), colistin (0.25 µg/ml, 0.5 µg/ml, 1.0 µg/ml, and 2.0 µg/ml), procaine (2500 µg/ml, 5000 µg/ml, 10,000 µg/ml, and 20,000 µg/ml), diamide (16.6 µg/ml, 33.3 µg/ml, 66.6 µg/ml, and 133 µg/ml), hydroxylamine (12 µg/ml, 25 µg/ml, 50 µg/ml, and 100 µg/ml), guanidine (500 µg/ml, 1000 µg/ml, 2000 µg/ml, and 4000 µg/ml), cupric chloride (20 µg/ml, 40 µg/ml, 80 µg/ml, and 160 µg/ml), zinc chloride (10 µg/ml, 20 µg/ml, 40 µg/ml, and 80 µg/ml), cadmium chloride (5.0 µg/ml, 10 µg/ml, 20 µg/ml, and 40 µg/ml), nickel chloride (20 µg/ml, 40 µg/ml, 80 µg/ml, and 160 µg/ml), chromium chloride (100 µg/ml, 200 µg/ml, 400 µg/ml, and 800 µg/ml), sodium selenite (100 µg/ml, 200 µg/ml, 300 µg/ml, and 400 µg/ml), potassium tellurite (0.2 µg/ml, 0.4 µg/ml, 0.8 µg/ml, and 1.6 µg/ml), manganese sulfate (100 µg/ml, 200 µg/ml, 400 µg/ml, and 800 µg/ml), cobalt chloride (12 µg/ml, 25 µg/ml, 50 µg/ml, and 100 µg/ml), silver chloride (2.0 µg/ml, 4.0 µg/ml, 8.0 µg/ml, and 16 µg/ml), potassium chromate (10 µg/ml, 20 µg/ml, 40 µg/ml, and 80 µg/ml), potassium bromide (225 µg/ml, 450 µg/ml, 900 µg/ml, and 1800 µg/ml), sodium cyanate (155 µg/ml, 310 µg/ml, 600 µg/ml, and 1200 µg/ml), sodium azide (500 µg/ml, 1000 µg/ml, 2000 µg/ml, and 4000 µg/ml), picolinic acid (50 µg/ml, 100 µg/ml, 200 µg/ml, and 400 µg/ml), potassium superoxide (100 µg/ml, 200 µg/ml, 400 µg/ml, and 800 µg/ml) and menadione (3.3 µg/ml, 6.6 µg/ml, 13.3 µg/ml, and 26.6 µg/ml).

The results of the first experiment indicated that in the presence of 10 µg/ml vancomycin, the E. coli strain tested exhibited transient increased sensitivity only to vancomycin at 10 µg/ml, 20 µg/ml, 40 µg/ml, and 80 µg/ml. In addition, the strain exhibited increased sensitivity to novobiocin at 33 µg/ml and 66 µg/ml, trimethoprim at 0.17 ng/ml, 0.33 ng/ml, 0.67 ng/ml, and 1.3 ng/ml, cefazolin at 2.0 µg/ml and 4.0 µg/ml, cephalothin at 10 µg/ml and 20 µg/ml, cefoxitin at 0.75 µg/ml and 1.5 µg/ml, fusidic acid at 200 µg/ml and 400

μg/ml, and nalidixic acid at 1.0 μg/ml, 2.0 μg/ml, and 4.0 μg/ml. Normal sensitivity levels were observed for the other tests in the ES1, ES2 and ES3 microarray panels.

The results also indicated that in the presence of 235 μg/ml sulfamethoxazole, the *E. coli* strain exhibited increased resistance to chlortetracycline at 0.25 μg/ml, 0.50 μg/ml, and 1.0 μg/ml, tetracycline at 0.033 μg/ml, 0.066 μg/ml, 0.133 μg/ml, and 0.266 μg/ml, novobiocin at 66 μg/ml and 133 μg/ml, but exhibited increased sensitivity to trimethoprim at 0.17 ng/ml, 0.33 ng/ml, 0.67 ng/ml, and 1.3 ng/ml, cephaloridine at 0.75 μg/ml, 1.5 μg/ml, 3.0 μg/ml, and 6.0 μg/ml, azomycin at 0.2 μg/ml, 0.4 μg/ml, 0.8 μg/ml, and 1.6 μg/ml, cefazolin at 0.5 μg/ml, 1.0 μg/ml, 2.0 μg/ml, and 4.0 μg/ml, cephalothin at 5.0 μg/ml, 10 μg/ml, and 20 μg/ml, cefaclor at 1.33 μg/ml, 2.66 μg/ml, and 5.33 μg/ml, cefsulodin at 8 μg/ml and 16 μg/ml, nickel chloride at 20 μg/ml and 40 μg/ml, chromium chloride at 200 μg/ml and 400 μg/ml, and cobalt chloride 12 μg/ml and 25 μg/ml. Normal sensitivity levels were observed for the other tests in the ES1, ES2 and ES3 microarray panels. Thus, this Example clearly illustrates the use of the present invention to test for synergy and/or antagonism using combinations of BACs.

EXAMPLE 2

Antimicrobial Testing

In this Example, experiments are described in which the feasibility of using PMs for analyzing the metabolic effects of antimicrobial compounds and their mechanisms of action were investigated. Specifically, the experiments were designed to determine whether compounds that act via interaction with specific bacterial proteins ("target-specific") can be distinguished from those acting via non-specific mechanisms, solely on the basis of differences in signature metabolic profiles. In addition, the experiments were designed to determine whether different interactors of the same pathway produce a similar signature profile, as well as whether interactors of different pathways produce distinctly different profiles.

Twenty chemicals were selected for inclusion in these experiments. Fifteen of these, listed below in Table 3 as "single target antimicrobials" are thought to have relatively specific modes of action, whereas five antimicrobials, listed as "multiple target antimicrobials" are thought to have non-specific modes of action. Among the single target compounds were three sets of antimicrobials with similar modes of action on the cell wall (ampicillin, cephalothin, phosphomycin, and bacitracin), ribosomes (chloramphenicol, streptomycin, and tetracycline), or DNA gyrases (nalidixic acid, oxolinic acid, and coumermycin).

An initial set of experiments was performed to select the concentrations of each chemical as it was desirable to use a partially inhibitory concentration. A completely inhibitory or sub-inhibitory concentration would not provide any information. Partial inhibitory levels were determined using the criterion of decreased formation of purple color due to inhibition of tetrazolium violet reduction (i.e., respiration). Each compound was tested at two concentrations giving partial inhibition of respiration. The lower concentration, referred to as "1x," was the lowest concentration giving detectable inhibition of respiration. The higher concentration, referred to as "2x," was twice the 1x concentration. For most chemicals, another doubling to 4x gave a completely inhibitory level that would not be useful. Thus, only 1x and 2x concentrations were used. It was determined that the selection of chemical concentration is an important parameter to control. However, the selection criteria used herein was found to be quite adequate. Only canavanine appeared to need a slightly higher concentration to give comparable results. If the concentration is chosen properly, only one concentration should be needed for the assay.

TABLE 3

Compounds Used and Their Modes of Action

| Compound | Target | Assumed Mode of Action |
| --- | --- | --- |
| Ampicillin | Single | Cell wall |
| Cephalothin | Single | Cell wall |
| Phosphomycin | Single | Cell wall |
| Bacitracin | Single | Cell wall |
| Polymyxin B | Single | Outer membrane |
| Cerulenin | Single | Membrane (fatty acid synthesis) |
| Chloramphenicol | Single | Ribosome |
| Streptomycin | Single | Ribosome |
| Tetracycline | Single | Ribosome, lipophilic chelator |
| Bleomycin | Single | DNA polymerase |
| Rifampicin | Single | RNA polymerase |
| Nalidixic Acid | Single | DNA gyrase |
| Oxolinic Acid | Single | DNA gyrase |
| Coumermycin | Single | DNA gyrase |
| Sulfathiazole | Single | Anti-folate |
| Sodium Dodecyl Sulfate (SDS) | Multiple | Membrane and protein denaturant |
| 5-Fluoro-Uracil (5-FU) | Multiple | Uracil analog |
| Canavanine | Multiple | Amino acid analog |
| N-ethyl Maleimide (NEM) | Multiple | Thiol reactive agent |
| Ethylmethane Sulfonate (EMS) | Multiple | Mutagen (alkylating agent) |

In these experiments, *E. coli* MG1655 was tested against 20 antimicrobials at two concentrations using 7 PMs each, for a total of 280 PMs. PMs without any antimicrobial (a set of 7) were run each day as a control (this total does not include data from the control strains). Since in these experiments each PM contains 95 phenotypes, the total number of phenotypes analyzed here was 26,600. Each PM was monitored kinetically every 15 minutes using a specialized instrument described is U.S. patent application Ser. No. 09/277,353 (herein incorporated by reference) for an incubation duration of 48 hours. Thus, the total number of data points for the experiments was 5,107,200. Bioinformatics software (Biolog™) as used to analyze these data.

The results of the data collected for a run is a kinetic phenotype of the cell exposed to an antimicrobial overlaid and compared against the phenotype of the cell without exposure to the antimicrobial. When the two kinetic tracings of tetrazolium reduction (i.e., cell respiration) overlap, there is no difference in the response to that phenotype (indicated as "O"). When the control tracing exceeds the antimicrobial tracing, the organism is scored as "more sensitive" or "S." When the antimicrobial tracing exceeds the control tracing, the organism is scored as "more resistant," or "R." Based on visual examination of the PMs after incubation, the threshold values for judging S and R results were determined. The software then automatically calculated the areas under the differential tracings and applied threshold values to score all 26,600 phenotypes as S, O, or R.

From the S—O—R data, a distance matrix was generated. The S—O—R response (a string of 665 values) for one antimicrobial was compared to the response for another antimicrobial, and the differences summed up. A difference of O to S or of O to R was assigned a value of 1, and a difference of S to R was assigned a value of 2. The string of 665 differences was then summed up. Pairs of antimicrobials with similar responses had lower difference values and pairs of antimicrobials with very different responses had higher difference values. The comparison of all pairs provides a distance matrix which can be used as input for algorithms that generate various cluster diagrams to help simplify and summarize the data.

Figure 4:
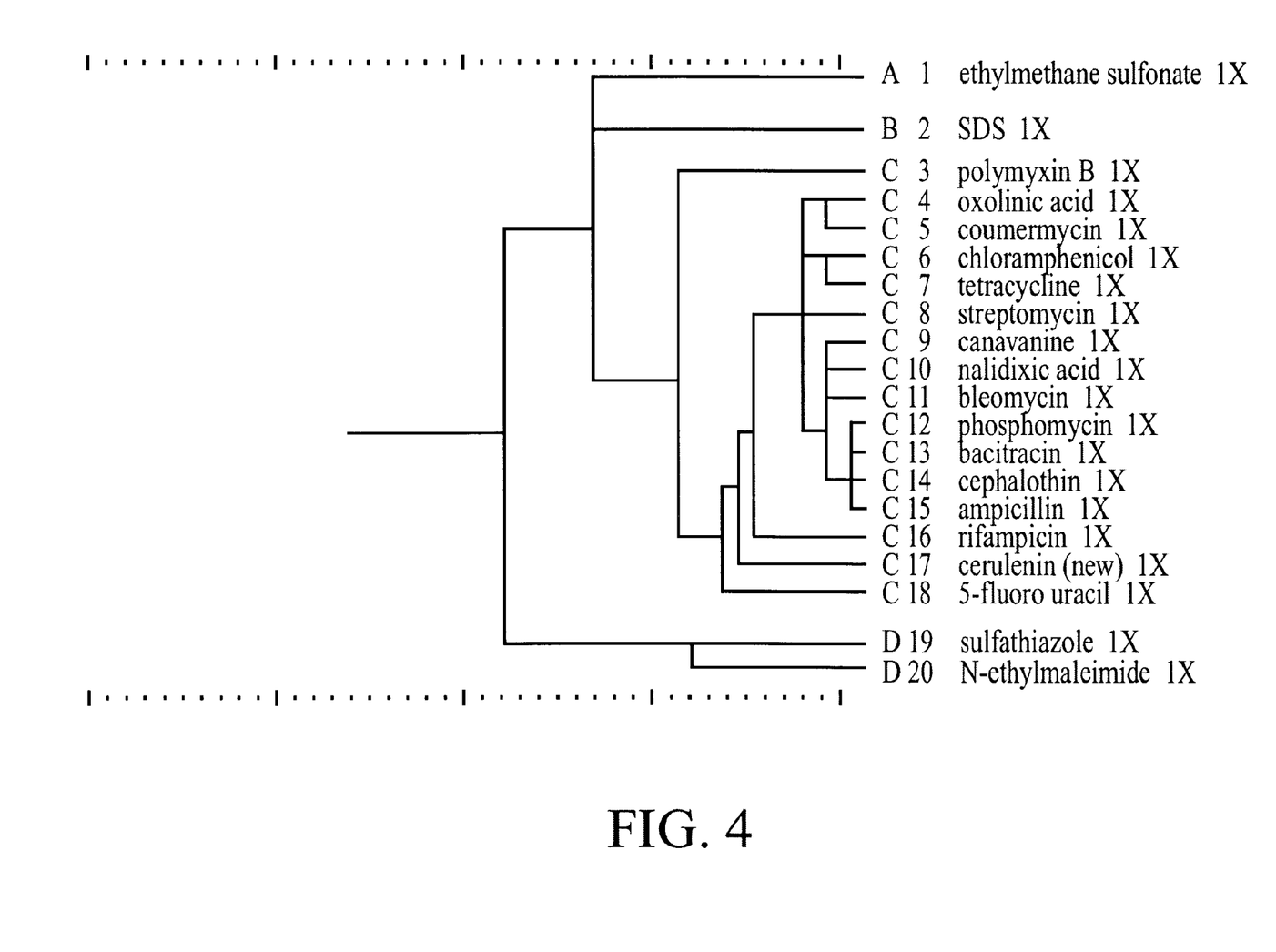
FIG. 4 provides a dendrogram showing the response of *E. coli* to various antimicrobials.

The results indicated a wide variation in the response of the organism to different classes of antimicrobials. For example, FIG. 4 shows a dendrogram of the data obtained at the 1x level of each antimicrobial. The four cell wall inhibitors (ampicillin, cephalothin, phosphomycin, and bacitracin) cluster, as do the three ribosome inhibitors (chloramphenicol, streptomycin, and tetracycline). Also, two out of the three of the DNA gyrase inhibitors (oxolinic acid and coumermycin) clustered. All of the single target antimicrobials except sulfathiazole and polymyxin B are in the tightly clustered center of the dendrogram, while all of the multiple target antimicrobials except canavanine are in the distant periphery of the dendrogram.

First, these results indicate that the present invention can be be used to differentiate single target from multiple target antimicrobials. The multiple target antimicrobials make cells broadly and non-specifically hypersensitive, whereas the single target antimicrobials have a more specific "fingerprint." Second, this fingerprint pattern appears to successfully permit grouping of antimicrobials based upon their mode of action and differentiates them from other antimicrobials with different modes of action.

In one case, the results were not as simple as expected. In this case, nalidixic acid did not cluster with the other two DNA gyrase inhibiting chemicals. This may indicate something about the mechanism of action of this drug. In addition, polymyxin B, cerulenin and sulfathiazole gave results that more closely resembled the multiple target antimicrobials. Polymyxin B and cerulenin both affect membrane synthesis and this may disrupt many cellular properties, as well as enhance the non-specific permeation of other antimicrobials.

EXAMPLE 3

BAC Testing of Yeast

In this Example, the response of a yeast to various compounds was tested. The yeast used in these experiments was Saccharomyces cerevisiae (BY4741, obtained from Dr. Mark Johnston, Washington University, St. Louis, Mo.). The genotype of this strain was indicated as being Mat a (i.e., mating type "a"), ura-, his-, leu-, and met-.

In these experiments, the ability of this strain to grow in a culture medium without methionine was investigated. Methionine interferes with the ability to test this organism for its utilization of other potential sulfur sources (i.e., if methionine is added to a culture medium the organism preferentially uses it as a sulfur source).

The yeast was grown for 48 hours at 30° C. on R2A agar medium (Acumedia). Cells were removed from the agar surface with a sterile cotton swab and suspended at a cell density of 65% transmittance (as read using a Biolog™ turbidimeter) in an inoculating fluid containing 50 mM glucose, 0.15 mM uracil, 0.15 mM L-histidine, 0.15 mM L-leucine, 0.15 mM $MgCl_2$, 1.0 mM $CaCl_2$, 2.0 mM NaCl, 1.0 mM KCl, 3.0 mM $NH_4Cl$, 1.0 mM $NaH_2PO_4$, 0.1 mM $Na_2SO_4$, 0.01% iodo-nitro-tetrazolium violet, 0.01% phyta-gel (gellan gum), 0.03% pluronic F-68; the pH was adjusted to 6.0.

The cell suspension (100 µl/well) was then used to inoculate a Biolog™ EA MicroPlate™, which tests the ability of a cell to be stimulated by a set of 95 different nutrients. The nutrients included within the microarray were: LB medium (10 g/L tryptone, 5 g/L yeast extract, and 5 g/L NaCl), L-alanine (25 µM), L-arginine (25 µM), L-asparagine (25 µM), L-aspartic acid (25 µM), L-cysteine (25 µM), L-glutamic acid (25 µM), adenosine 3',5'-cyclic monophosphate (100 µM), adenine (100 µM), adenosine (100 µM), 2'-deoxyadenosine (100 µM), L-glutamine (25 µM), glycine (25 µM), L-histidine (25 µM), L-isoleucine (25 µM), L-leucine (25 µM), L-lysine (25 µM), L-methionine (25 µM), L-phenylalanine (25 µM), guanosine 3',5'-cyclic monophosphate (100 µM), guanine (100 µM), guanosine (100 µM), 2'-deoxyguanosine (100 µM), L-proline (25 µM), L-serine (25 µM), L-threonine (25 µM), L-tryptophan (25 µM), L-tyrosine (25 µM), L-valine (25 µM), L-isoleucine and L-valine (25 µM each), trans-4-hydroxy L-proline (25 µM), (5) 4-aminoimidazole-4(5)-carboxamide (1 mM), hypoxanthine (100 µM), inosine (100 µM), 2'-deoxyinosine (100 µM), L-ornithine (100 µM), L-citrulline (100 µM), chorismic acid (100 µM), (−) shikimic acid (100 µM), L-homoserine lactone (100 µM), D-alanine (25 µM), D-aspartic acid (25 µM), D-glutamic acid (25 µM), DL-α,ε-diaminopimetic acid (25 µM), cytosine (100 µM), cytidine (100 µM), 2-deoxycytidine (100 µM), putrescine (25 µM), spermidine (25 µM), spermine (25 µM), pyridoxine (0.25 µM), pyridoxal (0.25 µM), pyridoxamine (0.25 µM), β-alanine (0.25 µM), D-pantothenic acid (0.25 µM), orotic acid (1 mM), uracil (100 µM), uridine (100 µM), 2'-deoxyuridine (100 µM), quinolinic acid (0.25 µM), nicotinic acid (0.25 µM), nicotinamide (0.25 µM), β-nicotinamide adenosine dinucleotide (0.25 µM), δ-aminolevulinic acid (0.25 µM), hematin (0.25 µM), deferoxamine mesylate (0.25 µM), glucose (I mM), N-acetyl-D-glucosamine (100 µM), thymine (100 µM), glutathione (reduced form; 100 µM), thymidine (100 µM), oxaloacetic acid (1 mM), d-biotin (0.25 µM), cyanobalamine (0.25 µM), p-aminobenzoic acid (0.25 µM), folic acid (0.25 µM), inosine (100 µM) and thiamine (25 µM), thiamine (0.25 µM), thiamine pyrophosphate (0.25 µM), riboflavin (0.25 µM), pyrrolo-quinoline quinone (0.25 µM), menadione (0.25 µM), myo-inositol (0.25 µM), butyric acid (100 µM), DL-α-hydroxybutyric acid (100 µM), α-ketobutyric acid (100 µM), caprylic acid (100 µM), DL-α-lipoic acid (oxidized form; 0.25 µM), DL-mevalonic acid (0.25 µM), DL-carnitine (0.25 µM), choline (0.25 µM), Tween-20 (0.01%), Tween-40 (0.01%), Tween-60 (0.01%), and Tween-80 (0.01%). One well (A-1) contains no nutrients and is used as a reference (i.e., control) well.

After inoculation, the microarray was incubated at 30° C. for 2 days and visually observed. Any well that contained nutrient that stimulated growth of the cells had a higher level of pink color due to increased cell respiration and reduction of the iodo-nitro-tetrazolium violet dye.

Three wells showed increased pink color. These wells were the wells which contained L-methionine, glutathione and pyridoxine. It was expected that methionine would be stimulatory, but it was unexpected that glutathione and pyridoxine would be stimulatory and could be used to substitute for methionine. In this case, because the ability of the organism to utilize various sulfur sources was being tested, glutathione could not be used as it also contains sulfur. However, pyridoxine does not contain sulfur, and could be used as a totally satisfactory replacement for methionine as a nutrient for S. cerevisiae strain BY4741. Thus, instead of growing and testing BY4741 on minimal media containing uracil, L-histidine, L-leucine, and L-methionine, it is possible to grow and test this strain on minimal media containing uracil, L-histidine, L-leucine, and pyridoxine.

From the above Examples, it is clear that the present invention represents an unexpected and much improved system for the broad-based, rapid phenotype array testing of microorganisms and/or other cell types with BACs, in many uses and formats (or configurations), as well as for antimicrobial development and research. In addition, both automated and manual systems with fixed time point or kinetic reading may be used in conjunction with the present invention. For example, the results may be observed visually (i.e., by eye) by the person conducting the test, without assistance from a machine. Alternatively, the results may be obtained with the use of equipment (e.g., a microtiter plate reader) that measures transmittance, absorbance, or reflectance through, in, or from each well of a multitest device such as a microtiter testing plate (e.g., MicroPlate™) or a miniaturized testing card (e.g., MicroCard™). Kinetic readings may be obtained by taking readings at frequent time intervals or reading the test results continuously over time. One example of a device particularly suited for incubating and conducting the methods of the present invention includes the device described in co-pending U.S. patent application Ser. Nos. 09/277,353, and 09/267,039, both of which are hereby incorporated by reference.

In embodiments utilizing the multitest gel-matrix, the invention provides numerous advances and advantages over the prior art, including: (1) much greater safety, as there is no spillage, nor aerosolization of cells, mycelia, nor spores, while performing or inoculating test wells; (2) faster biochemical reactions are produced, giving final results hours or days earlier than commonly used methods; (3) more positive biochemical or phenotypic reactions are obtained, giving a truer picture of the microorganisms' metabolic characteristics; (4) darker, more clear-cut biochemical reactions and color changes are obtained; (5) more uniform color and/or turbidity are obtained, as the cells, mycelia, and/or spores do not settle and clump together at the bottom of the wells, nor do they adhere to the sides of the wells; (6) the reactions are much easier to observe visually or with optical instruments (e.g., the Biolog MicroStation Reader™); and (7) the overall process for performing multiple tests is extremely simple and efficient, requiring very little labor on the part of the biologist. All of these advantages enhance the speed and accuracy of scoring test results in studies to perform comparative phenotype analysis for the assessment of BACs using any cell type, including microbial strains.

What is claimed is:

1. A method for testing the response of at least one cell to at least one biologically active chemical comprising the steps of:
   (a) providing:
      i) a testing device having at least two wells, wherein each well of said testing device contains at least one substrate selected from the group consisting of carbon sources, nitrogen sources, phosphorus sources, sulfur sources, growth stimulating nutrients, antimicrobials, and chromogenic testing substrates; and
      ii) a suspension comprising at least one cell and at least one biologically active chemical;
   (b) inoculating said suspension into said wells of said testing device; and
   (c) observing the response of said at least one cell to said at least one biologically active chemical.

2. The method of claim 1, wherein said testing device is selected from the group consisting of microtiter plates and microcards.

3. The method of claim 1, wherein said suspension further comprises a gelling agent.

4. The method of claim 1, wherein said testing device further comprises a gel-initiating agent in said wells.

5. The method of claim 1, wherein said suspension further comprises a colorimetric indicator.

6. The method of claim 1, wherein said testing device further comprises a colorimetric indicator in said wells.

7. The method of claim 1, wherein said observing is visual.

8. The method of claim 1, wherein said observing is performed by an instrument.

9. A method for comparing the effect of at least two biologically active chemicals comprising:
   a) providing:
      i) a first cell suspension comprising at least one cell type and at least one biologically active chemical,
      ii) a second cell suspension comprising the same said at least one cell type in step i) and at least one biologically active chemical wherein said biologically active chemical is different from said biologically active chemical in said first cell suspension,
      iii) a first testing device having wells, wherein said wells contain at least one substrate selected from the group consisting of carbon sources, nitrogen sources, phosphorus sources, sulfur sources, growth stimulating nutrients, antimicrobials, and chromogenic testing substrates,
      iv) a second testing device having wells, wherein said wells contain at least one substrate selected from the group consisting of carbon sources, nitrogen sources, phosphorus sources, sulfur sources, growth stimulating nutrients, antimicrobials, and chromogenic testing substrates, and
   b) adding said first cell suspension to said wells of said first testing device to provide a first phenotype array;
   c) adding said second cell suspension to said wells of said second testing device to provide a second phenotype array;
   d) incubating said first and said second phenotype arrays;
   e) observing the response of said cell suspension in said first and said second phenotype arrays; and
   f) comparing the response of said cell suspension in said first phenotype array with the response of said cell suspension in said second phenotype array.

10. The method of claim 9, wherein said first and second testing devices are selected from the group consisting of microtiter plates and microcards.

11. The method of claim 9, wherein said first and second cell suspensions further comprise a gelling agent.

12. The method of claim 9, wherein said first and second testing devices further comprise a gel-initiating agent in said wells.

13. The method of claim 9, wherein said first and second cell suspensions further comprise a calorimetric indicator.

14. The method of claim 9, wherein said first and second testing devices further comprise a colorimetric indicator in said wells.

15. The method of claim 9, wherein said first testing device contains the same substrates as said second testing device.

16. The method of claim 9, wherein said observing is visual.

17. The method of claim 9, wherein said observing is performed by an instrument.

18. The method of claim 9, wherein said comparison of said response is performed using multi-dimensional pattern analysis.

19. A multiwell kit for testing the effect of at least one biologically active chemical comprising: i) at least one testing device having at least two wells, wherein said wells contain at least one substrate selected from the group consisting of carbon sources, nitrogen sources, phosphorus sources, sulfur sources, growth stimulating nutrients, antimicrobials, and chromogenic substrates; and ii) a cell suspension medium containing at least one biologically active chemicals.

20. The method of claim 19, wherein said at least one testing device is selected from the group consisting of microtiter plates and microcards.

21. The kit of claim 19, wherein said cell suspension medium further comprises a gelling agent.

22. The kit of claim 19, wherein said testing device further comprises a gel-initiating agent in said wells.

23. The kit of claim 19, wherein said cell suspension medium further comprises a colorimetric indicator.

24. The kit of claim 19, wherein said testing device further comprises a colorimetric indicator in said wells.

* * * * *